(12) United States Patent
Chen et al.

(10) Patent No.: US 8,969,333 B2
(45) Date of Patent: Mar. 3, 2015

(54) THERAPEUTIC COMPOSITIONS AND METHODS

(71) Applicant: The Penn State Research Foundation, University Park, PA (US)

(72) Inventors: Gong Chen, State College, PA (US); Yanming Wang, State College, PA (US); Pingxin Li, State College, PA (US); Jing Hu, State College, PA (US); Shu Wang, State College, PA (US); Yuji Wang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/261,783

(22) Filed: Apr. 25, 2014

(65) Prior Publication Data
US 2014/0288059 A1 Sep. 25, 2014

Related U.S. Application Data

(62) Division of application No. 13/286,777, filed on Nov. 1, 2011, now Pat. No. 8,710,039.

(60) Provisional application No. 61/408,792, filed on Nov. 1, 2010.

(51) Int. Cl.
| | | |
|---|---|---|
| A61K 31/33 | (2006.01) |
| A61K 31/165 | (2006.01) |
| A61K 31/166 | (2006.01) |
| A61K 31/167 | (2006.01) |
| A61K 31/18 | (2006.01) |
| A61K 31/395 | (2006.01) |
| A61K 31/4188 | (2006.01) |
| A61K 31/47 | (2006.01) |
| A61K 31/496 | (2006.01) |
| A61K 31/4985 | (2006.01) |
| A61K 31/551 | (2006.01) |
| C07C 257/14 | (2006.01) |
| C07D 215/52 | (2006.01) |
| C07D 217/26 | (2006.01) |
| C07D 241/08 | (2006.01) |
| C07D 245/02 | (2006.01) |
| C07D 487/04 | (2006.01) |
| C07D 495/04 | (2006.01) |
| C12Q 1/34 | (2006.01) |
| A61K 31/472 | (2006.01) |
| A61K 31/4965 | (2006.01) |
| A61K 31/5513 | (2006.01) |
| A61K 45/06 | (2006.01) |
| C07D 215/48 | (2006.01) |
| C07D 243/14 | (2006.01) |

(52) U.S. Cl.
CPC ............ *A61K 31/165* (2013.01); *A61K 31/166* (2013.01); *A61K 31/167* (2013.01); *A61K 31/18* (2013.01); *A61K 31/33* (2013.01); *A61K 31/395* (2013.01); *A61K 31/4188* (2013.01); *A61K 31/47* (2013.01); *A61K 31/496* (2013.01); *A61K 31/4985* (2013.01); *A61K 31/551* (2013.01); *C07C 257/14* (2013.01); *C07D 215/52* (2013.01); *C07D 217/26* (2013.01); *C07D 241/08* (2013.01); *C07D 245/02* (2013.01); *C07D 487/04* (2013.01); *C07D 495/04* (2013.01); *C12Q 1/34* (2013.01); *A61K 31/472* (2013.01); *A61K 31/4965* (2013.01); *A61K 31/5513* (2013.01); *A61K 45/06* (2013.01); *C07D 215/48* (2013.01); *C07D 243/14* (2013.01)
USPC ........................................................ 514/183

(58) Field of Classification Search
USPC ........................................................ 514/183
See application file for complete search history.

(56) References Cited

U.S. PATENT DOCUMENTS

| | | | |
|---|---|---|---|
| 5,945,408 A | 8/1999 | Webber et al. |
| 5,981,511 A | 11/1999 | Gapud et al. |
| 6,207,708 B1 | 3/2001 | Gapud et al. |
| 2007/0276040 A1 | 11/2007 | Sato et al. |
| 2008/0199897 A1 | 8/2008 | Rahil et al. |
| 2009/0162877 A1 | 6/2009 | Thompson et al. |
| 2009/0306153 A1 | 12/2009 | Thompson et al. |
| 2010/0151506 A1 | 6/2010 | Thompson et al. |

FOREIGN PATENT DOCUMENTS

WO    WO-00/26195    5/2000

OTHER PUBLICATIONS

Blagosklonny et al 'Depletion of Mutant p53 and Cytotoxicity of Histone Deacetylase Inhibitors' Cancer Research, Vol., p. 7386-7392, 2005.*

Knuckley, B. et al., Profiling Protein Arginine Deiminase 4 (PAD4): A novel screen to identify PAD4 inhibitors, *Bioorg Med Chem*, 16(2): 739-45, Jan. 15, 2008 (Abstract only).

Knuckley, B. et al., A fluopol-ABPP HTS assay to identify PAD inhibitors, *Chem Commun (Camb)*, 46(38): 7175-7, Oct. 14, 2010 (Abstract only).

(Continued)

*Primary Examiner* — Wu-Cheng Winston Shen
*Assistant Examiner* — Christopher R Stone
(74) *Attorney, Agent, or Firm* — Gifford, Krass, Sprinkle, Anderson & Citkowski, P.C.

(57) ABSTRACT

PAD4 inhibitory compositions and methods for their use in treatment of cancer and autoimmune disease are provided according to embodiments of the present invention.

14 Claims, 19 Drawing Sheets

(56) References Cited

OTHER PUBLICATIONS

Knuckley, B. et al., Haloacetamidine-based inactivators of protein arginine deiminase 4 (PAD4): evidence that general acid catalysis promotes efficient inactivation, *Chembiochem*, 11(2): 161-5, Jan. 25, 2010 (Abstract only).

Knuckley, B. et al., Substrate specificity and kinetic studies of PADs, 1, 3, and 4 identify potent and selective inhibitors of protein arginine deiminase 3, *Biochemistry*, 49(23): 4852-63, Jun. 15, 2010 (Abstract only).

Li, P. et al., Regulation of p53 target gene expression by peptidylarginine deiminase 4, *Mol Cell Biol*, 28(15): 4745-58, Aug. 2008.

Luo, Y. et al., A Fluoroacetamidine-Based Inactivator of Protein Arginine Deiminase 4: Deiminase 4: Design, Synthesis, and in Vitro and in Vivo Evaluation, *J Am Chem Soc*, 128(4): 1092-3, Feb. 1, 2006.

Luo, Y. et al., Inhibitors and Inactivators of Protein Arginine Deiminase 4: Functional and Structural Characterization, *Biochemistry*, 45(39): 11727-36, Oct. 3, 2006.

Luo, Y. et al., Activity Based Protein Profiling Reagents for Protein Arginine Deiminase 4 (PAD4): Synthesis and in vitro Evaluation of a Fluorescently-labeled Probe, *J Am Chem Soc*, 128(45): 14468-69, Nov. 15, 2006.

Slack, J. et al., Protein arginine deiminase 4: a target for an epigenetic cancer therapy, *Cell Mol Life Sci*, Aug. 13, 2010.

Tanikawa, C. et al., Regulation of Protein Citrullination through p53/PADI4 Network in DNA Damage Response, *Cancer Res*, 69(22): 8761-69, Nov. 15, 2009.

Li, P. et al., Coordination of PAD4 and HDAC2 in the regulation of p53 target gene expression, Oncogene, 29(21): 3153-62, May 27, 2010.

Li, P. et al., PAD4 is essential for antibacterial innate immunity mediated by neutrophil extracellular traps, Journal of Experimental Medicine, 207(9): 1853-62, Aug. 23, 2010.

Chang, X. et al., Increased PADI4 expression in blood and tissues of patients with malignant tumors, BMC Cancer, 9(40), Jan. 2009.

* cited by examiner

THERAPEUTIC COMPOSITIONS AND METHODS

REFERENCE TO RELATED APPLICATION

This application is a divisional of U.S. patent application Ser. No. 13/286,777, filed Nov. 1, 2011, which claims priority from U.S. Provisional Patent Application Ser. No. 61/408,792, filed Nov. 1, 2010, the entire content of both of which is incorporated herein by reference.

GOVERNMENT SPONSORSHIP

This invention was made with government support under Grant No. R01 CA136856 awarded by the National Institutes of Health. The Government has certain rights in the invention.

FIELD OF THE INVENTION

The invention relates to compositions and methods for inhibiting peptidylarginine deiminase 4 (PAD4). Particular aspects relate to PAD4 inhibitors and methods for use in treatment of cancer and autoimmune disease.

BACKGROUND OF THE INVENTION

PAD4 is an enzyme that post-translationally converts peptidylarginine to citrulline. Over-expression of PAD4 has been linked to cancers and autoiummune disorders, such as rheumatoid arthritis and has been implicated in the pathogenesis of these diseases. There is a continuing need for PAD4 inhibitors and methods for their use in treatment of cancer and autoimmune disease.

SUMMARY OF THE INVENTION

Compositions are provided according to the present invention including a compound having the structural formula:

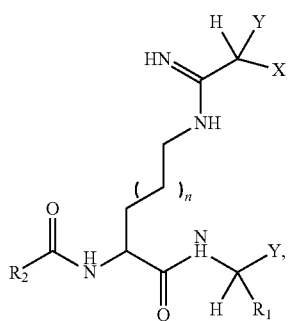

(I)

where n is 1 or 2; X is halogen; each Y is independently H, halogen, an O-linked aliphatic substituent or an N-linked aliphatic substituent; $R_1$ is an aliphatic or aromatic substituent; and R2 is an aliphatic or aromatic substituent; or a salt, stereoisomer, hydrate, amide or ester thereof.

Compositions are provided according to the present invention including a compound having the structural formula designated herein by the number (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof.

Compositions are provided according to the present invention including a compound having the structural formula: (I), where n is 1 or 2; X is halogen; each Y is independently halogen, an O-linked aliphatic substituent or an N-linked aliphatic substituent; $R_1$ is an aliphatic or aromatic substituent; and R2 is an aliphatic or aromatic substituent; or a structural formula designated herein by the number (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier.

Compositions are provided according to the present invention including a compound having the structural formula:

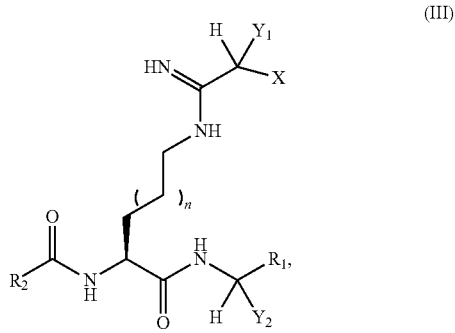

(III)

where n is 1 or 2; X is halogen; $Y_1$ and $Y_2$ are each independently H, halogen, an O-linked aliphatic substituent or an N-linked aliphatic substituent; $R_1$ is an aliphatic or aromatic substituent; and $R_2$ is an aliphatic or aromatic substituent; or a salt, stereoisomer, hydrate, amide or ester thereof; and optionally further including a pharmaceutically acceptable carrier.

Compositions are provided according to the present invention including a compound having the structural formula (III) wherein n is 1; $Y_1$ and $Y_2$ are both H; X is F or Cl; $R_1$ is an aliphatic or aromatic substituent; and $R_2$ is an aliphatic or aromatic substituent; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having the structural formula:

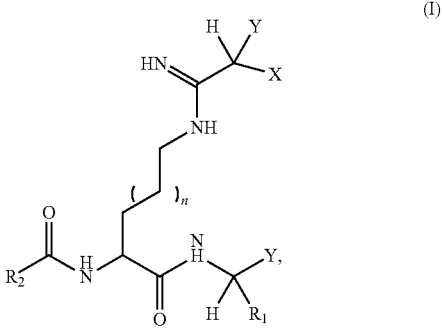

(I)

where n is 1 or 2; X is halogen; each Y is independently H, halogen, an O-linked aliphatic substituent or an N-linked aliphatic substituent; $R_1$ is an aliphatic or aromatic substituent; and $R_2$ is an aliphatic or aromatic substituent; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having the structural formula designated herein by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having the structural formula: (I), where n is 1 or 2; X is halogen; each Y is independently H, halogen, an O-linked aliphatic substituent or an N-linked aliphatic substituent; $R_1$ is an aliphatic or aromatic substituent; and R2 is an aliphatic or aromatic substituent; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having a structural formula designated herein by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having a structural formula:

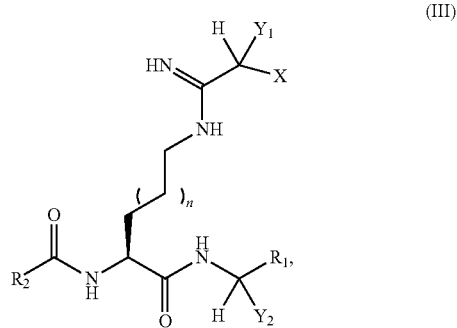

(III)

where n is 1 or 2; X is halogen; $Y_1$ and $Y_2$ are each independently H, halogen, an O-linked aliphatic substituent or an N-linked aliphatic substituent; $R_1$ is an aliphatic or aromatic substituent; and $R_2$ is an aliphatic or aromatic substituent; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having a structural formula (III) wherein n is 1; $Y_1$ and $Y_2$ are both H; X is F or Cl; $R_1$ is an aliphatic or aromatic substituent; and $R_2$ is an aliphatic or aromatic substituent; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor selected from the group consisting of: YW3-56, YW3-56F, YW3-56Br, YW-56A, YW3-56A-F, YW3-56A-Br; or a salt, stereoisomer, hydrate, amide or ester thereof; and optionally further including a pharmaceutically acceptable carrier.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject is human.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having cancer.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having cancer characterized by decreased levels or activity of one or more tumor suppressors.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having cancer characterized by decreased levels or activity of p53 tumor suppressor.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having cancer and wherein administering the therapeutically effective amount of the composition to a subject detectably increases autophagy and/or decreases proliferation of cells of the cancer.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having cancer; and further including administration of an additional therapeutic agent, an adjunct anti-cancer treatment or both an additional therapeutic agent and an adjunct anti-cancer treatment.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having cancer; and further including administration of a therapeutically effective amount of a histone deacetylase inhibitor.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof and optionally further including a pharmaceutically acceptable carrier, wherein the subject has or is at risk of having cancer; and further including administration of a therapeutically effective amount of SAHA.

Methods of treating a subject are provided according to embodiments of the present invention which include administering a therapeutically effective amount of a composition including a PAD4 inhibitor having a structural formula designated herein by the number (I) (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof; and optionally further including a pharmaceutically acceptable carrier, wherein the subject has or is at risk of having an autoimmune disease. Commercial packages are provided according to embodiments of the present invention which include one or more PAD4 inhibitors of the present invention having the structural formula designated herein by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof.

Commercial packages are provided according to embodiments of the present invention which include one or more PAD4 inhibitors of the present invention having the structural formula designated herein by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br; or a salt, stereoisomer, hydrate, amide or ester thereof and further including an ancillary component selected from the group consisting of: a pharmaceutically acceptable carrier, a buffer, a diluent and a reconstituting agent.

Methods for treating a subject with a PAD4 inhibitor are provided according to embodiments of the present invention including administering a composition including one or more PAD4 inhibitors having the structural formula designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; a salt, stereoisomer, hydrate, amide or ester thereof; and optionally further including a pharmaceutically acceptable carrier.

Assay methods are provided according to embodiments of the present invention which include contacting a cell with a fluorescent PAD4 inhibitor and detecting fluorescence of the PAD4 inhibitor.

Assay methods are provided according to embodiments of the present invention which include contacting a cell with a fluorescent PAD4 inhibitor selected from the group consisting of: YW3-56, YW3-56F, YW3-56Br, YW3-56A, YW3-56A-F, YW3-56A-Br and YW4-15; salt, stereoisomer, hydrate, amide or ester thereof.

DETAILED DESCRIPTION OF THE INVENTION

Figure 1:
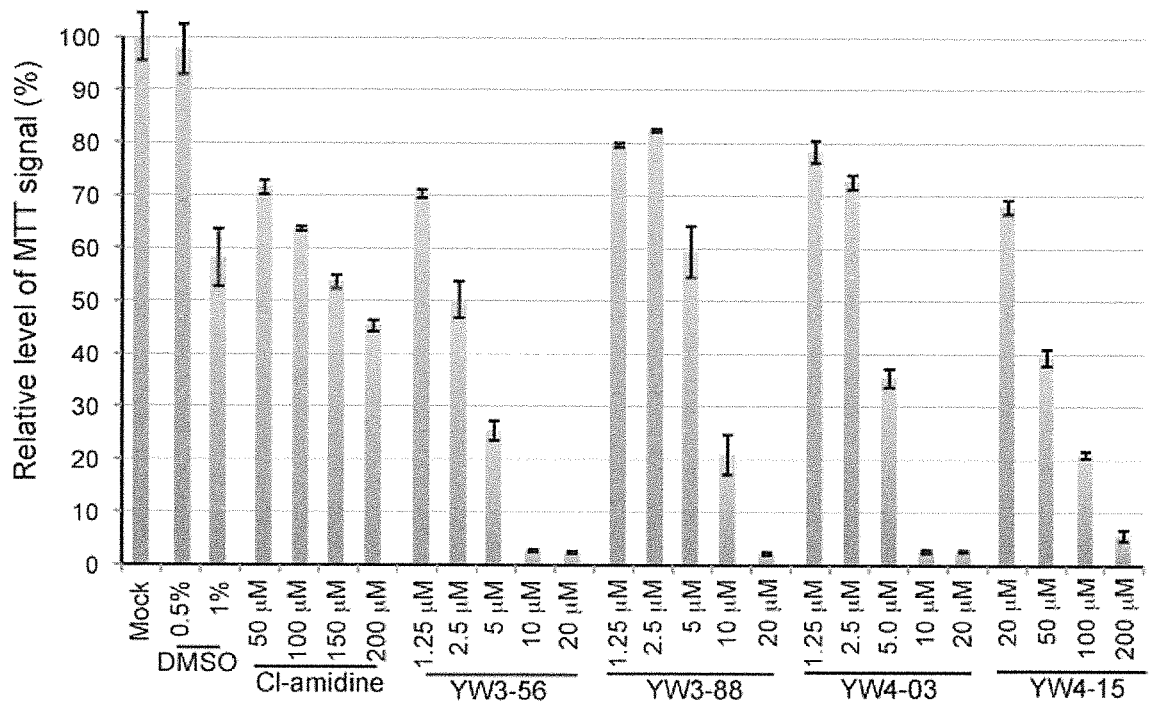
FIG. 1 is a graph showing results of MTT assays conducted to evaluate activity of compounds to inhibit cancer cell growth.

The singular terms "a," "an," and "the" include plural referents unless the context clearly indicates otherwise.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2006; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 11th Ed., 2005.

PAD4 inhibitory compositions and methods for their use in treatment of cancer and autoimmune disease are provided according to embodiments of the present invention.

A composition provided according to embodiments of the present invention includes one or more compounds having the structural formula:

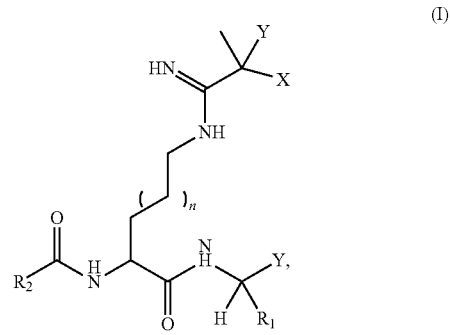

(I)

where n is 1 or 2; X is halogen; each Y is independently H, halogen, an O-linked aliphatic substituent or an N-linked aliphatic substituent; $R_1$ is an aliphatic or aromatic substituent; and $R_2$ is an aliphatic or aromatic substituent. $R_1$ and $R_2$ are tethered together in a ring structure in some compounds of the present invention.

Compositions according to the present invention encompass stereoisomers of chemical structures shown and/or described herein. Compositions according to the present invention encompass the individual enantiomers of the compounds having chemical structures shown and/or described herein, such as structures designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F and YW3-56A-Br as shown or described herein; as well as wholly or partially racemic mixtures of any of these.

A composition provided according to embodiments of the present invention includes one or more compounds having the structural formula:

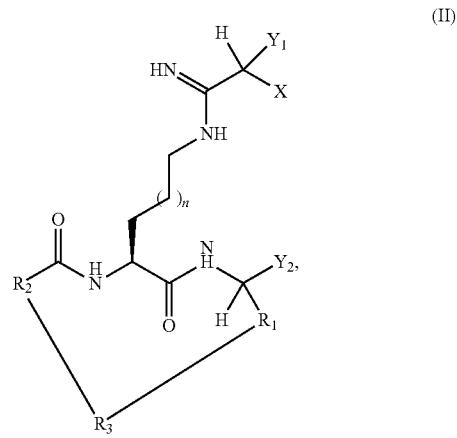

(II)

where n is 1 or 2; X is halogen; $Y_1$ and $Y_2$ are each independently H, halogen, an O-linked aliphatic substituent or an N-linked aliphatic substituent; $R_1$ is an aliphatic or aromatic substituent; $R_2$ is an aliphatic or aromatic substituent; and $R_3$ is a 4-9 carbon substituted or unsubstituted, straight chain, branched or cyclic hydrocarbon group.

A composition provided according to embodiments of the present invention includes one or more compounds having the structural formula:

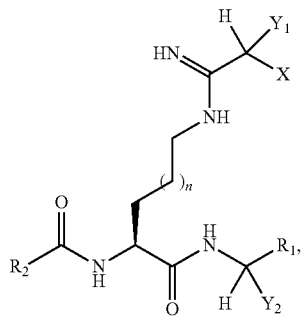

(III)

where n is 1 or 2; X is halogen; $Y_1$ and $Y_2$ are each independently H, halogen, an O-linked aliphatic substituent or an N-linked aliphatic substituent; $R_1$ is an aliphatic or aromatic substituent; and $R_2$ is an aliphatic or aromatic substituent.

A composition provided according to embodiments of the present invention includes one or more compounds having the structural formula:

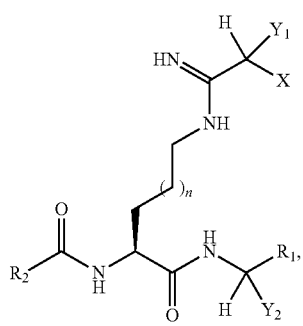

(III)

where n is 1; X is F or Cl; $Y_1$ is H; $Y_2$ is H; $R_1$ is an optionally substituted aromatic or heteroaromatic substituent; and $R_2$ is an optionally substituted aromatic or heteroaromatic substituent.

The term "aromatic" as used herein refers to an optionally substituted monocyclic or bicyclic aromatic or heteroaromatic ring system. Non-limiting examples of aromatic substituents include phenyl, benzyl and napthyl, each of which may be a heteroaromatic group. An aromatic substituent may itself be substituted at any substitutable position and may have 1-the maximum number of substituents. As a non-limiting example, an aromatic substituent may itself be substituted at any substitutable position by a C1-C4 optionally substituted hydrocarbon group, halogen, nitro, cyano, optionally substituted amino, hydroxy or oxo.

The term "aliphatic" as used herein refers to a substituted or unsubstituted straight chain or branched hydrocarbon group. Illustrative examples of aliphatic groups are methyl, ethyl, iso-propyl, n-propyl, n-butyl, iso-butyl, sec-butyl and tert-butyl. An aliphatic substituent may itself be substituted at any substitutable position and may have 1-the maximum number of substituents. As a non-limiting example, an aliphatic substituent may itself be substituted at any substitutable position by a C1-C4 optionally substituted hydrocarbon group, halogen, nitro, cyano, optionally substituted amino, hydroxy or oxo.

The term "halogen" as used herein refers to F, Cl, Br or I, preferably F or Cl.

Compositions including mixtures of two or more PAD4 inhibitors of the present invention are also specifically contemplated and are considered to be within the scope of the present invention.

Structures of particular PAD4 inhibitors of the present invention, are shown below.

Structure 3, also referred to as YW1-28:

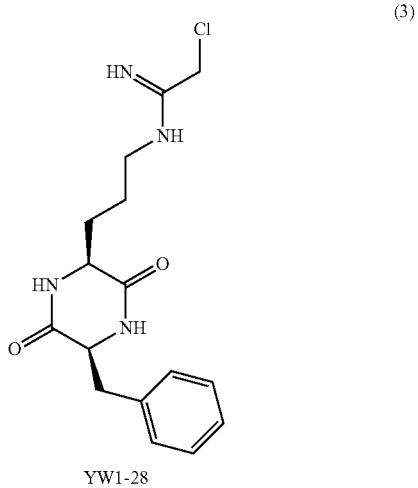 [SMILES: N=C(CCl)NCCC[C@@H]1NC(=O)[C@H](Cc2ccccc2)NC1=O]

(3)

YW1-28

Structure 4, also referred to as YW1-44:

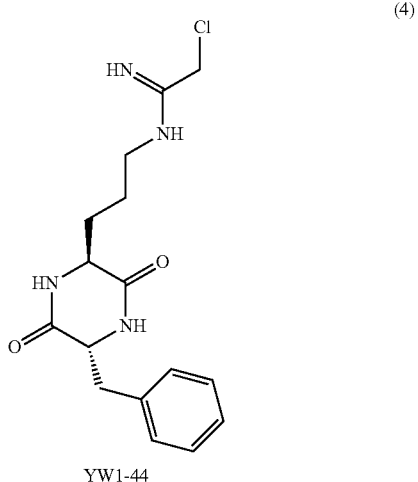 [SMILES: N=C(CCl)NCCC[C@@H]1NC(=O)[C@@H](Cc2ccccc2)NC1=O]

(4)

YW1-44

Structure 5, also referred to as YW1-30:

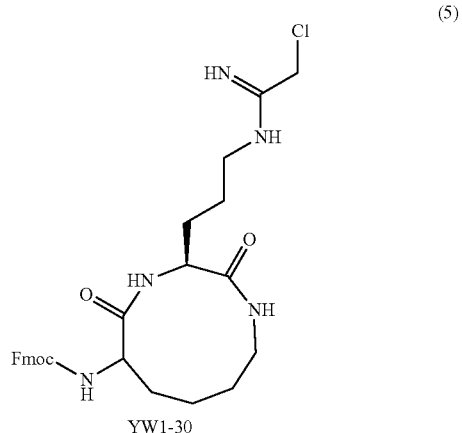

(5)

YW1-30

Structure 6, also referred to as YW1-49:
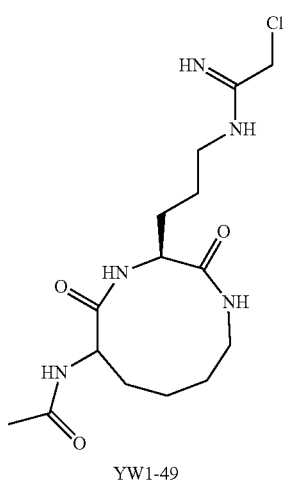
(6)
Structure 7, also referred to as BL1-26:
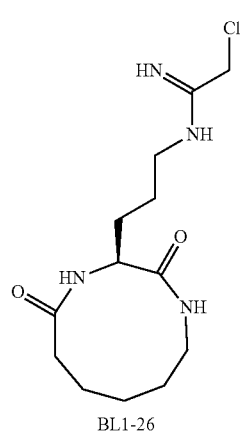
(7)
Structure 8, also referred to as YW1-90:
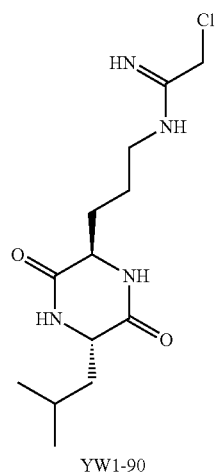
(8)
Structure 9, also referred to as YW1-91:
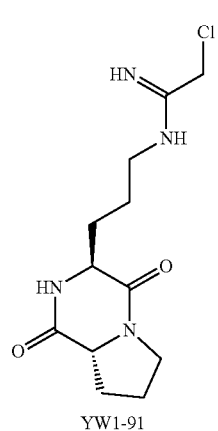
(9)
Structure 10, also referred to as YW1-94:
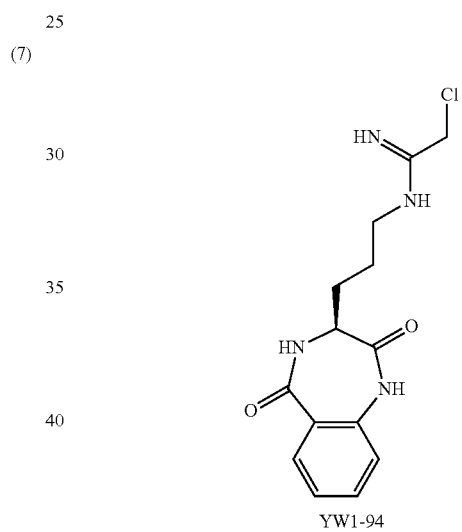
(10)
Structure 11, also referred to as YW1-98:
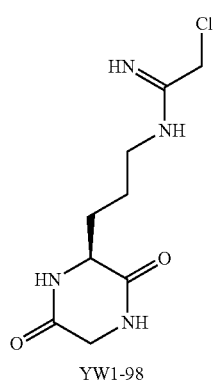
(11)

Structure 12, also referred to as BL1-07:
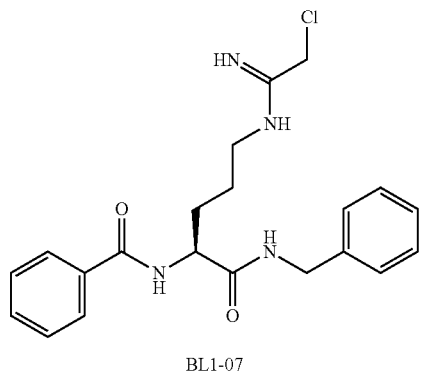
BL1-07
Structure 13, also referred to as BL1-15:
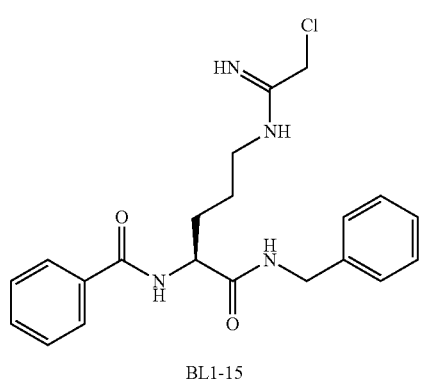
BL1-15
Structure 15, also referred to as YW3-88:
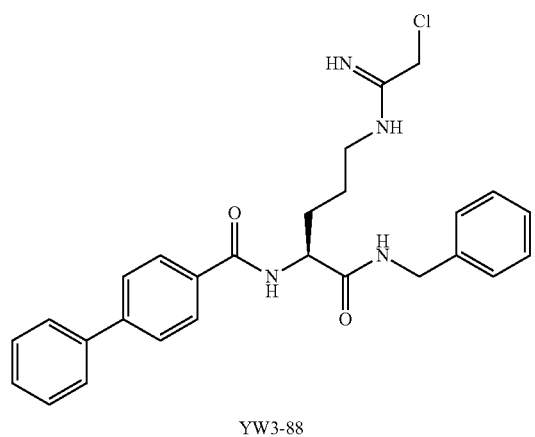
YW3-88
Structure 16, also referred to as YW4-03:
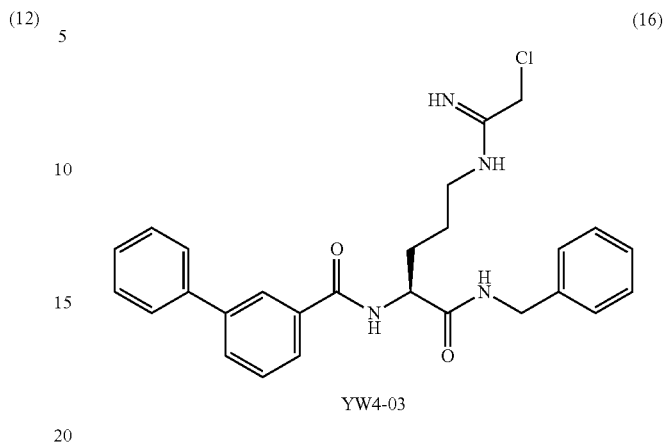
YW4-03
Structure 17, also referred to as YW4-06:
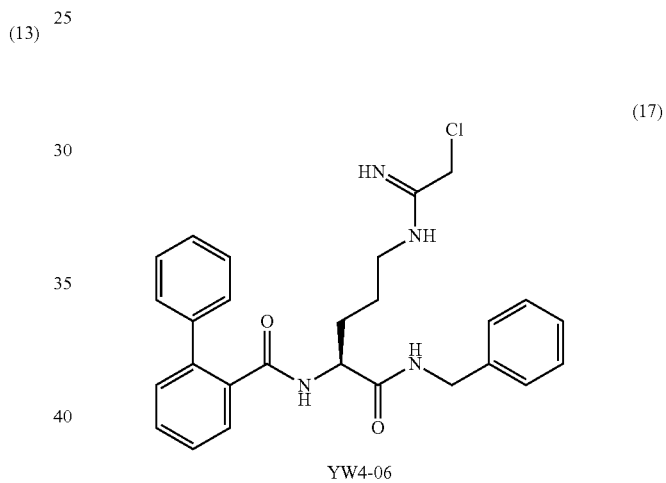
YW4-06
Structure 18, also referred to as YW3-64:
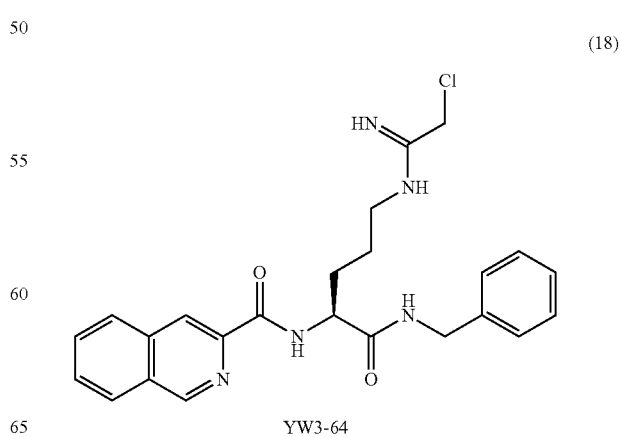
YW3-64

Structure 19, also referred to as YW3-75
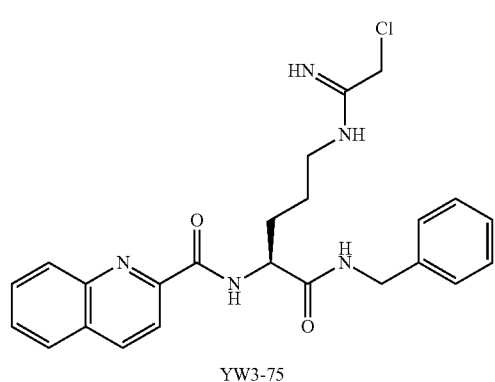
YW3-75
Structure 20, also referred to as YW3-56:
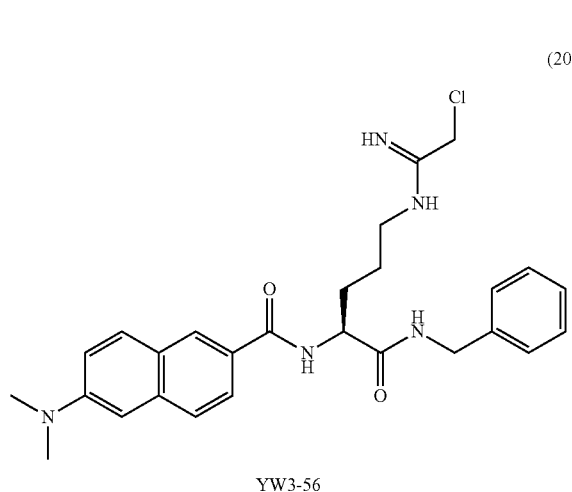
YW3-56
Structure 21, also referred to as YW3-71:
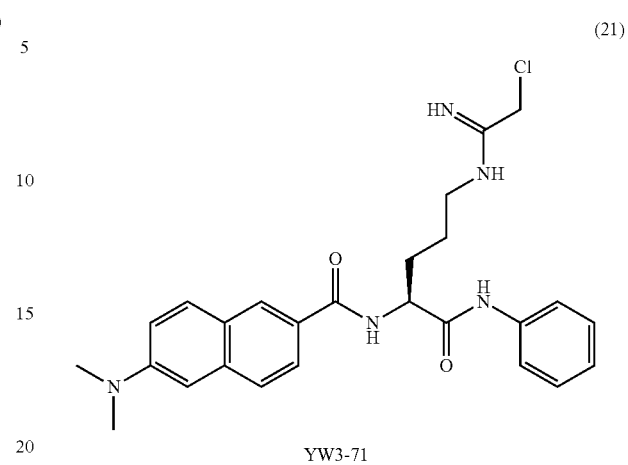
YW3-71
Structure 23, also referred to as YW3-92:
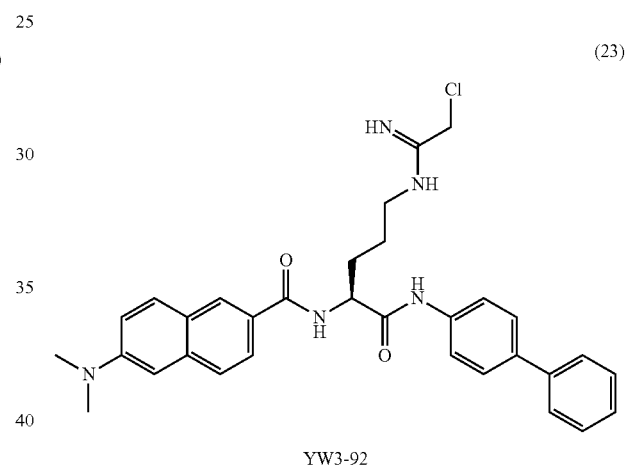
YW3-92
Structure 24, also referred to as YW4-15:
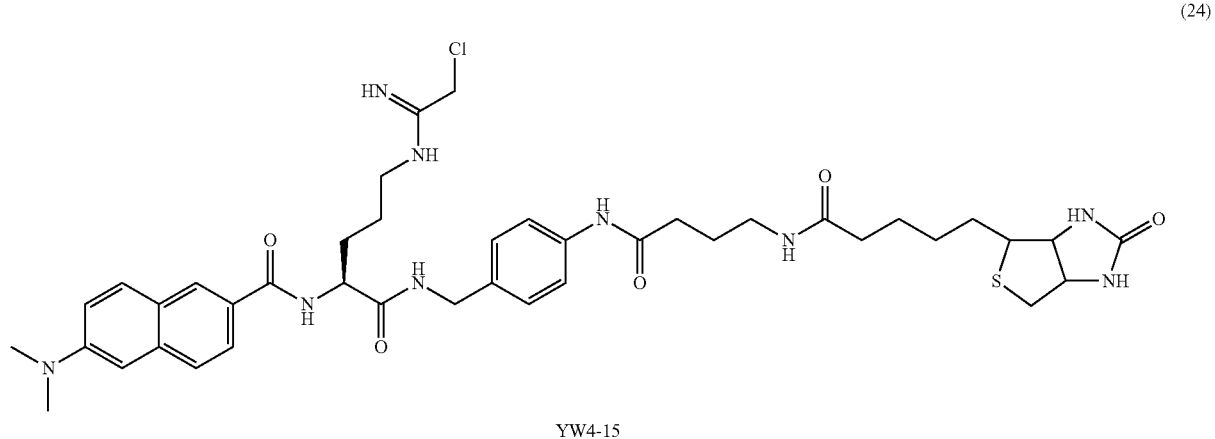 [SMILES: CN(C)c1ccc2cc(C(=O)N[C@@H](CCCNC(=N)CCl)C(=O)NCc3ccc(NC(=O)CCCNC(=O)CCCCC4SCC5NC(=O)NC54)cc3)ccc2c1]
YW4-15

A composition provided according to embodiments of the present invention includes one or more compounds having the structural formula designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; or a salt, stereoisomer, hydrate, amide or ester thereof.

The term "PAD4 inhibitor" as used herein refers to the activity of compositions of the present invention to specifically reduce the enzymatic activity of PAD4. As noted above, PAD4 is an enzyme that post-translationally converts peptidylarginine to citrulline. Assays to identify and characterize the specific inhibitory activity of a PAD4 inhibitor are known, as exemplified herein and in Knuckley et al., Bioorg. Med. Chem., 16(2):739-45 (2008).

PAD4 inhibitors of the present invention are synthesized using well-known chemical synthesis methodology. Exemplary methods for synthesis of PAD4 inhibitors of the present invention are described in Examples included herein.

According to embodiments of the present invention, a composition is provided including PAD4 inhibitor (20), also designated compound YW3-56; as well as salts, stereoisomers, hydrates, amides and esters thereof.

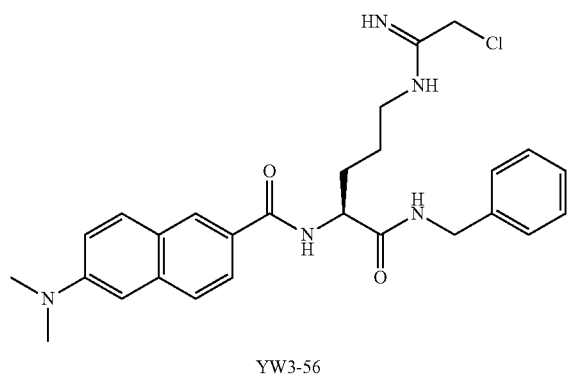 [SMILES: CN(C)c1ccc2cc(C(=O)N[C@@H](CCCNC(=N)CCl)C(=O)NCc3ccccc3)ccc2c1]

YW3-56

According to further embodiments, the Cl in PAD4 inhibitor (20) YW3-56 is F or Br. The Cl in PAD4 inhibitor (20) YW3-56 is replaced with F as shown in PAD4 inhibitor designated YW3-56F.

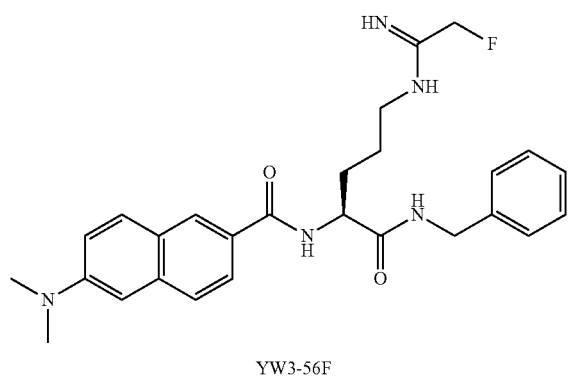 [SMILES: CN(C)c1ccc2cc(C(=O)N[C@@H](CCCNC(=N)CF)C(=O)NCc3ccccc3)ccc2c1]

YW3-56F

Similarly, the Cl in PAD4 inhibitor (20) YW3-56 is replaced with Br in a PAD4 inhibitor designated YW3-56Br.

According to further embodiments, the phenyl group in PAD4 inhibitor (20) YW3-56 is substituted. For example, the phenyl group in PAD4 inhibitor (20) YW3-56 is substituted with N3 as shown in PAD4 inhibitor designated YW3-56A.

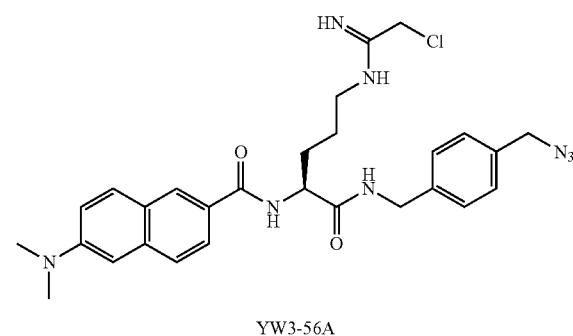 [SMILES: CN(C)c1ccc2cc(C(=O)N[C@@H](CCCNC(=N)CCl)C(=O)NCc3ccc(CN=[N+]=[N-])cc3)ccc2c1]

YW3-56A

The Cl in PAD4 inhibitor YW3-56A may be replaced with F or Br, resulting in YW3-56A-F and YW3-56A-Br, respectively.

PAD4 inhibitors 20 and 24, YW3-56 and YW4-15, respectively, YW3-56F, YW3-56Br, YW3-56A, YW3-56A-F and YW3-56A-Br are intrinsically fluorescent and are therefore useful in PAD4 inhibitor detection applications such as, but not limited to, detecting and monitoring cell and tissue uptake of these PAD4 inhibitors along with intracellular localization and detection and monitoring of the effects of PAD4 inhibitors on cells treated with the PAD4 inhibitors.

Assay methods are provided according to embodiments of the present invention which include contacting a cell with a fluorescent PAD4 inhibitor and detecting fluorescence of the PAD4 inhibitor.

Methods of Treatment

PAD4 inhibitor compositions according to embodiments of the present invention inhibit cancer cell growth and tumor growth and are useful as chemotherapeutic agents for treatment of cancer.

The term "cancer" as used herein includes solid tumors, hematolgic tumors and/or malignancies, pre-neoplastic hyperproliferation, cancer in-situ, neoplasms and metastases. Inhibitors of PAD4 according to embodiments of the present invention have utility in treatment of subject having cancer or at risk of having cancer such as skin cancers, cancers of the liver, prostate, breast, brain, stomach, pancreas, blood cells, uterus, cervix, ovary, lung, colon, connective tissues (sarcomas) and other soft tissues.

Many autoimmune diseases, such as rheumatoid arthritis, multiple sclerosis, and autoimmune nephritis, involve the immune response to self-antigens carrying citrullinated-peptides of self-derived peptides. PAD4 inhibitors of the present invention are administered to treat an autoimmune disease in a subject according to embodiments of the present invention.

Methods and compositions are provided according to the present invention for treating cancer and autoimmune disease. The terms "treating" and "treatment" used to refer to treatment of a cancer or an autoimmune disease in a subject include: preventing, inhibiting or ameliorating the cancer or autoimmune disease in the subject, such as slowing progression of the cancer or autoimmune disease and/or reducing or ameliorating a sign or symptom of the cancer or autoimmune disease. Thus, methods and compositions of the present invention can be used for prophylaxis as well as amelioration of signs and/or symptoms of cancer or autoimmune disease.

Methods of treating a subject having, or at risk of having, cancer or an autoimmune disease are provided according to embodiments of the present invention, which include administering a therapeutically effective amount of a PAD4 inhibitor of the present invention to the subject.

Methods of treating a subject having, or at risk of having, cancer or an autoimmune disease are provided according to embodiments of the present invention, which include administering a therapeutically effective amount of a PAD4 inhibitor having the structure designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; a salt, stereoisomer, hydrate, amide or ester thereof of the present invention to the subject.

Subjects are identified as having, or at risk of having, a cancer or an autoimmune disease using well-known medical and diagnostic techniques.

A therapeutically effective amount of a composition is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, or other condition responsive to a PAD4 inhibitor, a therapeutically effective amount of a composition is effective to ameliorate or prevent one or more signs and/or symptoms of the condition. For example, a therapeutically effective amount of a composition is effective to detectably increase autophagy and/or decrease proliferation of cells of a cancer including, but not limited to, pre-neoplastic hyperproliferation, cancer in-situ, neoplasms, metastasis, a tumor or other condition characterized by abnormal cell proliferation responsive to a PAD4 inhibitor.

In particular embodiments, cancers treated using methods and compositions described herein are characterized by decreased tumor supressors, such as p53.

Decreased levels or activity of one or more tumor supressors is determined, for instance, by measurement of gene copy number, protein or RNA levels in cells known or suspected to be dysplasic, pre-cancerous, cancerous, metastatic or otherwise characterized by abnormal cell proliferation compared to normal cells. Assays for decreased levels or activity of one or more tumor supressors include, but are not limited to immunoassays and nucleic acid assays.

Methods of treating a subject are provided according to embodiments of the present invention which include administering a therapeutically effective amount of a composition including a PAD4 inhibitor to a subject in need thereof, wherein the PAD4 inhibitor has the structure designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; a salt, stereoisomer, hydrate, amide or ester thereof and wherein the subject has or is at risk of having a condition characterized by decreased levels or activity of one or more tumor supressors, such as cancer, exemplified by pre-neoplastic hyperproliferation, cancer in-situ, neoplasms, metastasis or tumor.

Methods of treating a subject are provided according to embodiments of the present invention which include administering a therapeutically effective amount of a composition including a PAD4 inhibitor to a subject in need thereof, wherein the PAD4 inhibitor has structure designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; a salt, stereoisomer, hydrate, amide or ester thereof and wherein the subject has or is at risk of having cancer, exemplified by pre-neoplastic hyperproliferation, cancer in-situ, neoplasms, metastasis or tumor.

Methods of treating a subject are provided according to embodiments of the present invention which include administering a therapeutically effective amount of a composition including a PAD4 inhibitor to a subject in need thereof, wherein the PAD4 inhibitor has structure designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; a salt, stereoisomer, hydrate, amide or ester thereof and wherein the subject has or is at risk of having cancer, exemplified by pre-neoplastic hyperproliferation, cancer in-situ, neoplasms, metastasis or tumor, characterized by increased PAD4 compared to a corresponding healthy cells or tissue. Such cancers characterized by increased PAD4 compared to a corresponding healthy cells or tissue are known, as described for example in Chang, X et al., BMC Cancer. 9:40, 2009. Cancers characterized by increased PAD4 levels and/or activity compared to a corresponding healthy cells or tissue can also be identified by obtaining a sample from a subject and performing an assay to assess PAD4 in the sample compared to a control by any of various standard assay techniques such as immunological or molecular biology methods exemplified by immunocytochemistry, Western blot, PCR and ELISA.

Methods including administration of one or more PAD4 inhibitors of the present invention to a subject in need thereof are provided according to particular embodiments of the present invention which have utility, for example, in altering cell signaling pathways epigenetically for disease treatment.

Methods of modulating a tumor suppressor gene in a cell are provided according to embodiments of the present invention which include contacting the cell with an effective amount of a PAD4 inhibitor.

Methods of treating a subject are provided according to embodiments of the present invention which include administering a therapeutically effective amount of a composition including a PAD4 inhibitor to a subject in need thereof, wherein the PAD4 inhibitor has structure designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; a salt, stereoisomer, hydrate, amide or ester thereof and wherein the subject has, or is at risk of having, an autoimmune disease characterized by an immune response to self-antigens carrying citrullinated-peptides of self-derived peptides, exemplified by but not limited to, rheumatoid arthritis, multiple sclerosis, and autoimmune nephritis.

Combination Treatments

Combinations of therapeutic agents are administered according to embodiments of the present invention. In some embodiments, two or more PAD4 inhibitors of the present invention selected from the group are administered to a subject to treat cancer or an autoimmune disease in a subject in need thereof. In further embodiments, at least one PAD4 inhibitor of the present invention and at least one additional therapeutic agent are administered to a subject to treat cancer or an autoimmune disease in a subject in need thereof. In still further embodiments, at least one PAD4 inhibitor of the present invention and at least two additional therapeutic agents are administered to a subject to treat cancer or an autoimmune disease in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in embodiments of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

An additional therapeutic agent is an anti-cancer agent according to embodiments. Anti-cancer agents are described, for example, in Goodman et al., Goodman and Gilman's The Pharmacological Basis of Therapeutics, 8th Ed., Macmillan Publishing Co., 1990.

Anti-cancer agents illustratively include, antimetabolites, alkylating agents, acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

A particular additional therapeutic agent included in combination therapies according to embodiments of the present invention is a histone deacetylase (HDAC) inhibitor, exemplified by suberoylanilide hydroxamic acid (SAHA).

An additional therapeutic agent can be a radiation treatment of a subject or an affected area of a subject's body.

Combination therapies utilizing one or more PAD4 inhibitors of the present invention and one or more additional therapeutic agents may show synergistic effects, e.g., a greater therapeutic effect than would be observed using either the one or more PAD4 inhibitors of the present invention or one or more additional therapeutic agents alone as a monotherapy.

In particular, administration of one or more PAD4 inhibitors of the present invention and SAHA is found to provide a synergistic therapeutic anti-cancer effect.

According to embodiments, combination therapies include: (1) pharmaceutical compositions that include one or more PAD4 inhibitors of the present invention in combination with one or more additional therapeutic agents; and (2) co-administration of one or more PAD4 inhibitors of the present invention with one or more additional therapeutic agents wherein the one or more PAD4 inhibitors of the present invention and the one or more additional therapeutic agents have not been formulated in the same composition. When using separate formulations, the one or more PAD4 inhibitors of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the one or more PAD4 inhibitors of the present invention and the one or more additional therapeutic agents used in methods of the present invention.

Pharmaceutical Compositions

Pharmaceutical compositions including a PAD4 inhibitor of the present invention are also provided according to embodiments of the present invention. Pharmaceutical compositions of the present invention may be formulated in a conventional manner using one or more pharmaceutically acceptable carriers and/or excipients.

A pharmaceutical composition includes a PAD4 inhibitor of the present invention and a pharmaceutically acceptable carrier in particular embodiments of the present invention. The term "pharmaceutically acceptable carrier" refers to a carrier which is substantially non-toxic to a subject to which the composition is administered and which is substantially chemically inert with respect to a PAD4 inhibitor of the present invention.

A pharmaceutical composition according to the invention generally includes about 0.1-99% of a PAD4 inhibitor of the present invention. Combinations of PAD4 inhibitors in a pharmaceutical composition are also considered within the scope of the present invention.

Optionally, a method of treating a subject having cancer or at risk of having cancer further includes an adjunct anti-cancer treatment. An adjunct anti-cancer treatment can be administration of an anti-cancer agent or other additional therapeutic agent. An adjunct anti-cancer treatment can be a radiation treatment of a subject or an affected area of a subject's body.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, a compound of the present invention is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular embodiments, compositions of the present invention are formulated for topical application.

A topical formulation can be an ointment, lotion, cream or gel in particular embodiments. Topical dosage forms such as ointment, lotion, cream or gel bases are described in Remington: The Science and Practice of Pharmacy, $21^{st}$ Ed., Lippincott Williams & Wilkins, 2006, p. 880-882 and p. 886-888; and in Allen, L. V. et al., Ansel's Pharmaceutical Dosage Forms and Drug Delivery Systems, $8^{th}$ Ed., Lippincott Williams & Wilkins, 2005, p. 277-297.

Pharmaceutically acceptable carriers, excipients and formulation of pharmaceutical compositions are known in the art, illustratively including, but not limited to, as described in Remington: The Science and Practice of Pharmacy, 21 Ed., Lippincott, Williams & Wilkins, Philadelphia, Pa., 2006; and Allen, L. V. et al., Ansel's Pharmaceutical Dosage Forms and Drug Delivery Systems, $8^{th}$ Ed., Lippincott, Williams & Wilkins, Philadelphia, Pa., 2005.

The term subject refers to an individual in need of treatment for a pathological condition, particularly cancer and/or an autoimmune disease, and generally includes mammals and birds, such as, but not limited to, humans, other primates, cats, dogs, cows, horses, rodents, pigs, sheep, goats and poultry. According to embodiments, a subject in need of treatment for a pathological condition, particularly cancer and/or an autoimmune disease is a human.

A pharmaceutical composition according to the present invention is suitable for administration to a subject by a variety of systemic and/or local routes including, but not limited to, intravenous, intramuscular, subcutaneous, intraperitoneal, intraarterial, intracardiac, intradermal, intraarticular, transtracheal, subcuticular, subcapsular, subarachnoid, intraspinal, intrasternal, oral, buccal, otic, rectal, vaginal, topical, transdermal, parenteral, pulmonary, ocular, nasal, intratumoral and mucosal.

An inventive composition may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for chronic treatment of cancer.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

PAD4 inhibitors according to embodiments of the present invention are formulated to augment lipid-solubility and/or aqueous-solubility.

In particular embodiments, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular embodiments, a particulate carrier is formulated such that particles have an average particle size in the range of about 1 nm-100 nm.

Commercial Packages

Commercial packages are provided according to embodiments of the present invention for treating cancer or an autoimmune disease in a subject in need thereof, including one or more PAD4 inhibitors of the present invention having the structural formula designated by the number (I), (II), (III), 3, 4, 5, 6, 7, 8, 9, 10, 11, 12, 13, 15, 16, 17, 18, 19, 20, 21, 23, 24, YW3-56F, YW3-56Br, YW3-56A, YW3-56A-F or YW3-56A-Br as shown or described herein; or a salt, stereoisomer, hydrate, amide or ester thereof. One or more auxiliary components are optionally included in commercial packages of the present invention, such as a pharmaceutically acceptable carrier exemplified by a buffer, diluent or a reconstituting agent.

Embodiments of inventive compositions and methods are illustrated in the following examples. These examples are provided for illustrative purposes and are not considered limitations on the scope of inventive compositions and methods.

EXAMPLES

Example 1

Solution phase synthetic methods are used to produce PAD4 inhibitors of the present invention having the formula:

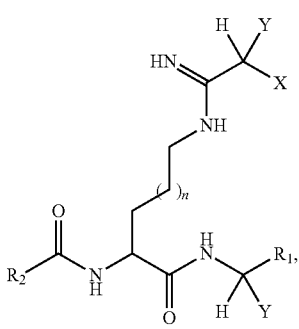

(III)

where n is 1 or 2; X is halogen; each Y is independently H, halogen, an O-linked aliphatic substituent or an N-linked aliphatic substituent; $R_1$ is an aliphatic or aromatic substituent; and $R_2$ is an aliphatic or aromatic substituent.

To produce inhibitors of structure (III), aromatic and aliphatic substituents with varied steric and hydrophobic properties are attached to the C terminus of L-ornithine (Orn) as shown in Scheme 1, below. Different building blocks bearing hydroxyl or amino functional groups are attached to the side chain amino group of Orn via standard ester or amide coupling chemistry.

Example 2

Solid phase synthetic methods can be used to produce PAD4 inhibitors of the present invention having the structural formula:

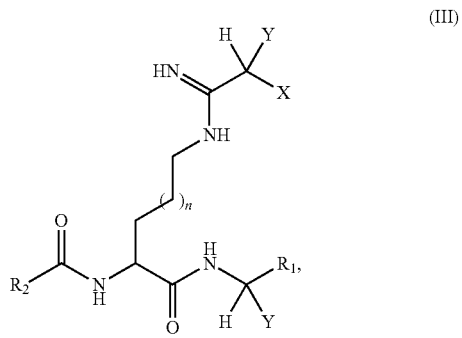

(III)

where n is 1 or 2; X is halogen; each Y is independently H, halogen, an O-linked aliphatic substituent or an N-linked aliphatic substituent; R1 is an aliphatic or aromatic substituent; and R2 is an aliphatic or aromatic substituent.

In this example, an L-ornithine starting material bearing the Fmoc-Nα and Dmab-Cα is firstly prepared in large quantity in solution phase and then immobilized onto the chlorotrityl resin via its ε-amine side chain. Fmoc and Dmab protecting groups are selectively removed for the subsequent installation of $R1NH_2$ and $R2CO_2H$ via standard amide coupling chemistry. Upon detachment from resin under acidic treatment, the resulting amine intermediate reacts with the ethyl chloroacetamidine (or fluoroacetamidine) to provide the desired final product. A purification procedure, such as a chromatography purification procedure can be used. This method can be used to produce PAD4 inhibitory compounds of the present invention.

Example 3

A representative synthesis of YW 3-56 is shown in synthetic Scheme 1.

Scheme 1:

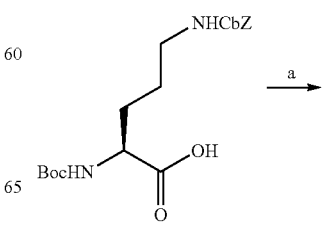

-continued

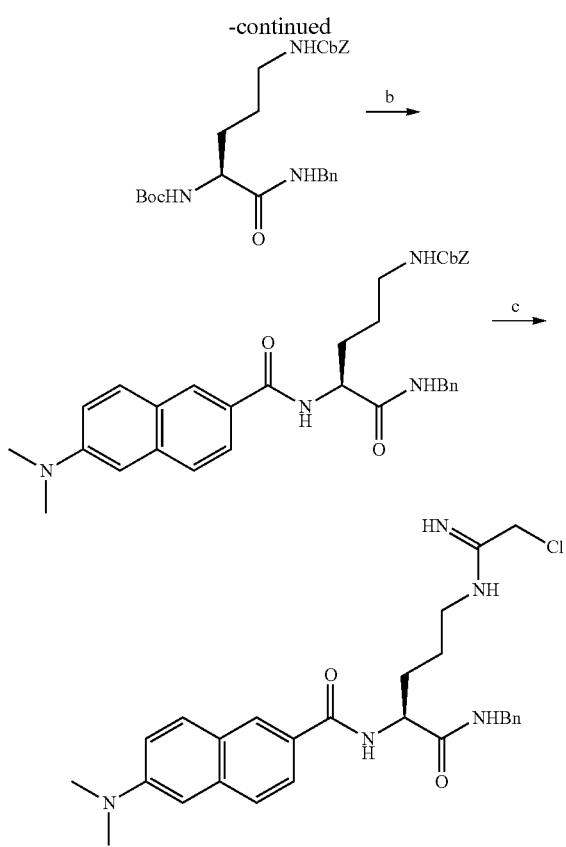

Reagents and Conditions:
a) BnNH2, EDCI, HOBt, DIPEA, DMF, room temperature (rt), 4 hr, 83% yield.
b) 20% TFA in dichloromethane, rt, 4 hr; 6-(dimethylamino)-2-naphthoic acid, EDCI, HOBt, DIPEA, DMF, rt, 74% yield in two steps.
c) H2, Pd/C, MeOH, rt; ethyl chloroacetamidate. MeOH, rt, 52% yield in two steps.

Generally described in this synthesis, a properly protected BocOrn(Cbz)OH is coupled with benzyl amine (BnNH$_2$) via an EDCI-mediated amide coupling reaction. The Boc protecting group of the coupled product is then removed under TFA acidic treatment and the resulting free amino group is coupled with dimethylaminonaphthoic acid by EDCI. This coupled intermediate is then treated with catalytic hydrogenation to remove the Cbz protecting group of the side chain amino group, which then reacts with ethyl chloroacetamidate to give the final product YW3-56 in good yield. This method can be used to produce PAD4 inhibitory compounds of the present invention.

In a specifically described example of this synthesis, a mixture of BocOrn(Cbz)OH (1.0 g, 2.73 mmol), Benzyl amine (684 mg, 4.10 mmol), EDCI (780 mg, 4.10 mmol), DIPEA (1.056 g, 8.09 mmol) in DMF (60 ml) was stirred at room temperature for 4 hours. The solvent was evaporated in vacuo, the residue was dissolved in 50 ml of ethyl acetate, the resulting solution was washed successively with saturated aqueous solution of NaHCO$_3$ (30 ml×3), 5% aqueous solution of KHSO$_4$ (30 ml×3) and saturated aqueous solution of NaCl (30 ml×3) and dried over anhydrous Na$_2$SO$_4$. After filtration, the filtrate was evaporated in vacuo and the crude material was purified by flash chromatography (silica gel: 230-400 mesh; 25% ethyl acetate/Hexane as eluent) to give the title compound as white solid. Yield: 1.03 g (83%).

To a solution of BocOrn(Cbz)NHBn (1.03 g, 2.26 mmol) in anhydrous DCM (10 ml) was added TEA (2 ml) at 0° C., and the temperature was increased slowly to room temperature, and then stirred for 4 h. The solvent and was removed under N$_2$ flow. The crude product was used in the next step without further purification.

A mixture of HOm(Cbz)NHBn (100 mg, 0.225 mmol), 6-(dimethylamino)-2-naphthoic acid (42 mg, 0.195 mmol), EDCI (45 mg, 0.235 mmol), DIPEA (76 mg, 0.588 mmol) in DMF (10 ml) was stirred at room temperature for 4 hours. The solvent was evaporated in vacuo, the residue was dissolved in 20 ml of ethyl acetate. The solution was washed successively with saturated aqueous solution of NaHCO$_3$ (10 ml×3), 5% aqueous solution of KHSO$_4$ (10 ml×3) and saturated aqueous solution of NaCl (10 ml×3) and dried over anhydrous Na$_2$SO$_4$. After filtration the filtrate was evaporated in vacuo and the crude material was purified by flash chromatography (silica gel: 230-400 mesh; 5% methanol/DCM as eluent) to give the title compound as white solid. Yield: 85 mg (74% in two steps).

To the solution of (S)-benzyl 5-(benzylamino)-4-(6-(dimethylamino)-2-naphthamido)-5-oxopentylcarbamate (80 mg, 0.145 mmol) in methanol (10 ml) of was added Pd/C (10%) 10 mg. The reaction mixture was stirred under H$_2$ balloon for 8 hr at rt. After filtration the filtrate was evaporated in vacuo and the residue was triturated with ether repeatedly to provide (S)—N-(5-amino-1-(benzylamino)-1-oxopentan-2-yl)-6-(dimethylamino)-2-naphthamide as colorless powder.

A mixture of (S)—N-(5-amino-1-(benzylamino)-1-oxopentan-2-yl)-6-(dimethylamino)-2-naphthamide (78 mg, 0.186 mmol), ethyl chloroacetamidate (110 mg, 0.90 mmol), TEA (150 µl), in MeOH (4 ml) was stirred at room temperature for 24 hours. The solvent was evaporated in vacuo, the residue was dissolved in 20 ml of ethyl acetate, the resulting solution was washed successively with saturated aqueous solution of NaHCO$_3$ (10 ml×3) and saturated aqueous solution of NaCl and dried over anhydrous Na$_2$SO$_4$. After filtration the filtrate was evaporated in vacuo and the crude material was purified by flash chromatography (silica gel: 230-400 mesh; 5% methanol/DCM as eluent) to give the title compound as pale yellow solid. Yield: 47.6 mg (52% in two steps).

The detailed scheme described for compound YW 3-56 can be used to synthesize other compounds of the present invention with minor routine modifications to achieve the desired compound.

Example 4

A representative synthesis of YW 3-53 is shown in synthetic Scheme 2:

Scheme 2:

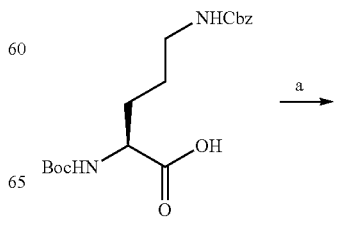

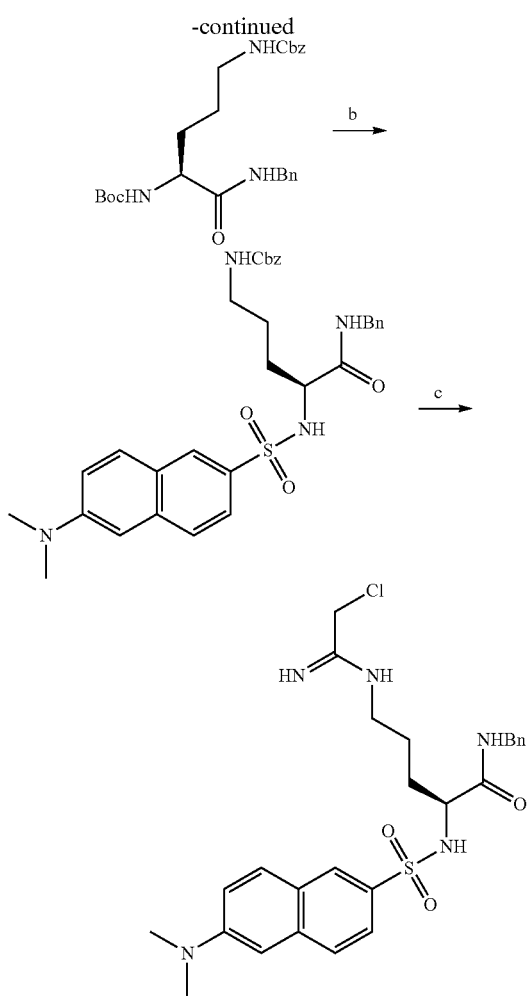

Reagents and Conditions:

a) BnNH$_2$, EDCI, HOBt, DIPEA, DMF, room temperature (rt), 4 hr, 83% yield.

b) 20% TFA in dichloromethane, rt, 4 hr, 2-Dimethylaminonaphthalene-6-sulfonyl chloride, TEA, DMF, THF, rt, 74% yield in two steps.

c) H2, Pd/C, MeOH, rt, ethyl chloroacetamidate, MeOH, rt, 46% yield in two steps.

A mixture of Orn(Cbz)NHBn (76 mg, 0.282 mmol), 2-Dimethylaminonaphthalene-6-sulfonyl chloride (92 mg, 0.235 mmol), TEA (114 mg, 1.128 mmol) in DMF (1 ml) and THF (4 ml) was stirred at room temperature for 2 hours. The solvent was evaporated in vacuo, the residue was dissolved in 20 ml of ethyl acetate, the solution was washed successively with saturated aqueous solution of NaHCO$_3$ (10 ml×3), 5% aqueous solution of KHSO$_4$ (10 ml×3) and saturated aqueous solution of NaCl (10 ml×3) and dried over anhydrous Na$_2$SO$_4$. After filtration the filtrate was evaporated in vacuo and the crude material was purified by flash chromatography (silica gel: 230-400 mesh; 5% methanol/DCM as eluent) to give the title compound as white solid. Yield: 116 mg (70% in two steps).

To the solution of (S)-benzyl 5-(benzylamino)-4-(6-(dimethylamino)naphthalene-2-sulfonamido)-5-oxopentylcarbamate (23 mg, 0.039 mmol) in methanol (5 ml) of was added Pd/C (10%) 5 mg. The reaction mixture was stirred under H$_2$ balloon for 8 h at rt. After filtration the filtrate was evaporated in vacuo and the residue was triturated with ether repeatedly to provide (S)-5-amino-N-benzyl-2-(6-(dimethylamino)naphthalene-2-sulfonamido)pentanamide as colorless powder.

A mixture of (S)-5-amino-N-benzyl-2-(6-(dimethylamino)naphthalene-2-sulfonamido)pentanamide (20 mg, 0.044 mmol), ethyl chloroacetamidate (15 mg, 0.095 mmol), TEA (20 µl), in MeOH (4 ml) was stirred at rt for 24 hours. The solvent was evaporated in vacuo, the residue was dissolved in 20 ml of ethyl acetate, the formed solution was washed successively with saturated aqueous solution of NaHCO$_3$ (10 ml×3) and saturated aqueous solution of NaCl and dried over anhydrous Na$_2$SO$_4$. After filtration the filtrate was evaporated in vacuo and the crude material was purified by flash chromatography (silica gel: 230-400 mesh; 5% methanol/DCM as eluent) to give the title compound as pale yellow solid. Yield: 10 mg (46% in two steps).

The detailed scheme described for compound YW 3-53 can be used to synthesize other compounds of the present invention with minor routine modifications to achieve the desired compound.

Example 5

A representative synthesis of YW 4-15 is shown in synthetic Scheme 3:

Scheme 3:

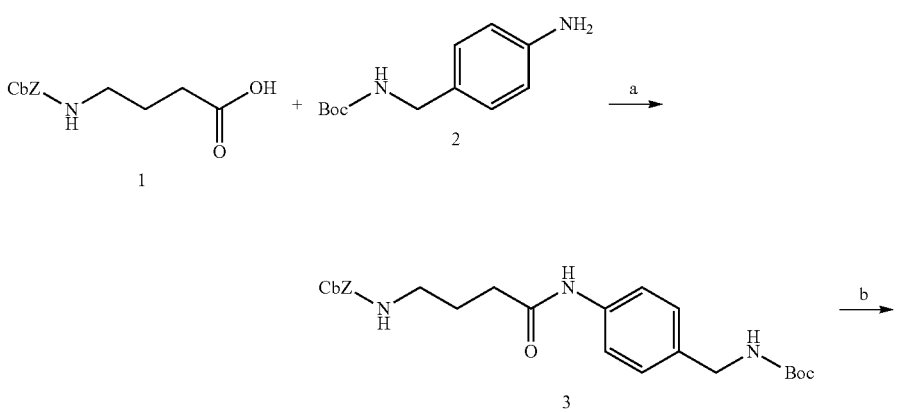

-continued
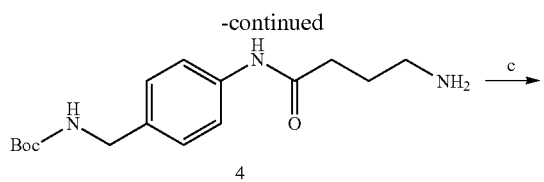
4
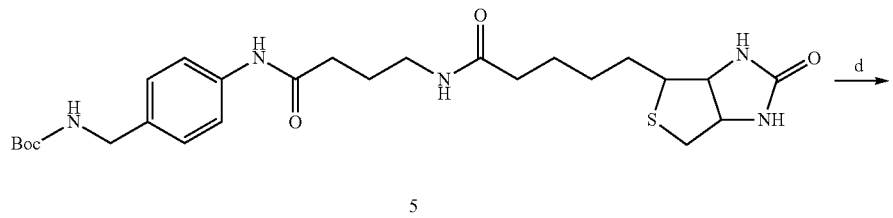
5
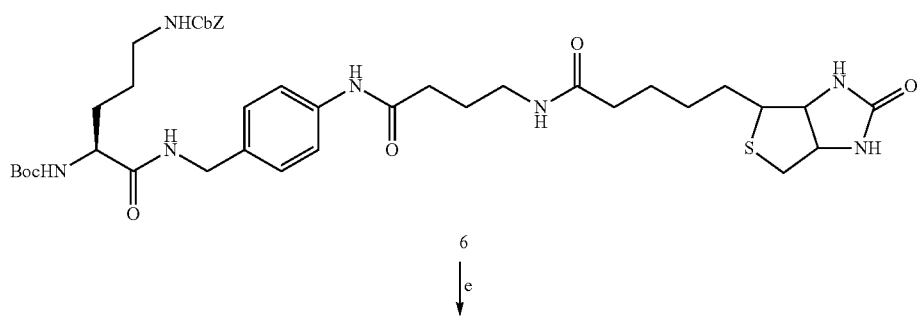
6
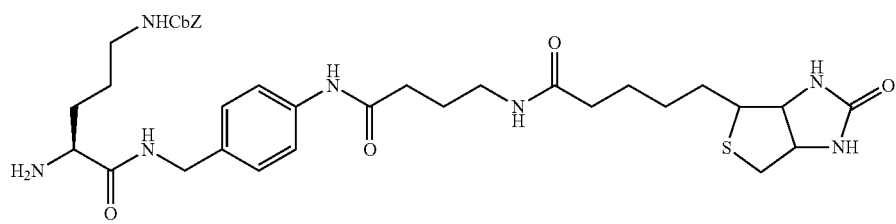
7
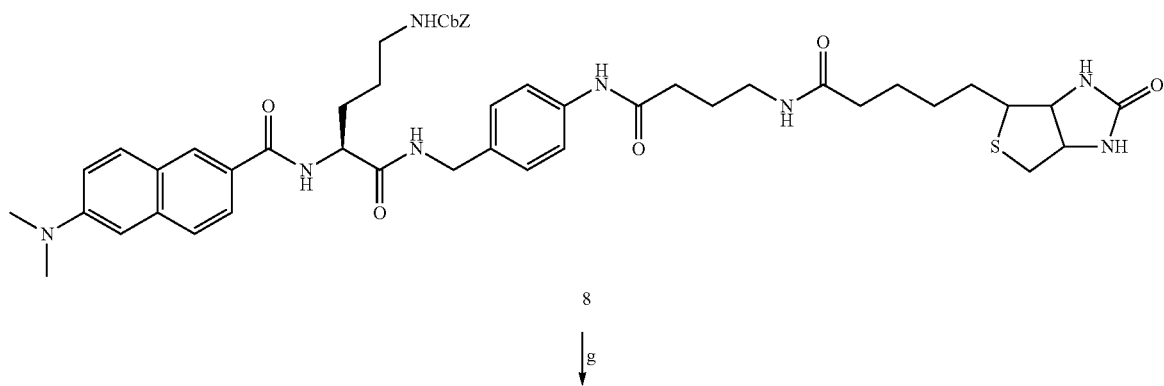
8

-continued

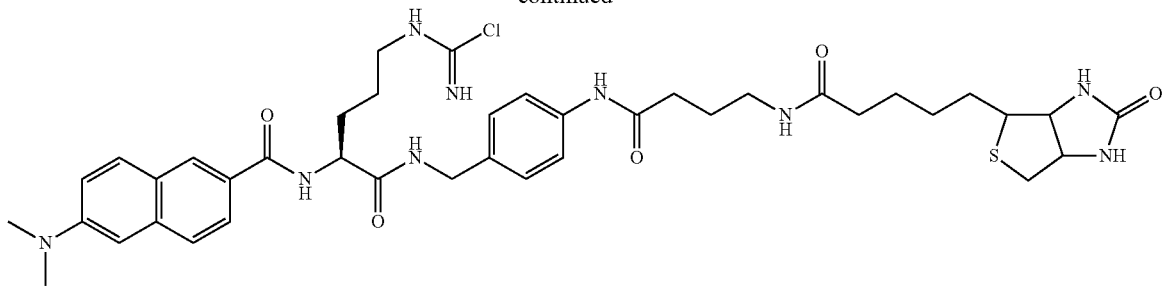

9

Reagents and Conditions:
a) HATU, DIPEA, DMF, room temperature (rt), 4 hr, 90% yield.
b) H₂, Pd/C, MeOH, rt, 12 hr, 90% yield.
c) Biotin, HATU, DIPEA, DMF, room temperature (rt), 2 hr, 77% yield
d) 20% TFA in dichloromethane, rt, 2 hr, BocOrn(Cbz)OH, HATU, DIPEA, DMF, room temperature (rt), 2 hr, 90% yield
e) 20% TFA in dichloromethane, rt, 2 hr
f) 6-(dimethylamino)-2-naphthoic acid,, DIPEA, DMF, room temperature (rt), 4 hr, 85% yield
g) H₂, Pd/C, MeOH, rt, ethyl chloroacetamidate, MeOH, rt, 50% yield in two steps.

A mixture of 4-{[(benzyloxy)carbonyl]amino}butanoic acid (260 mg, 1.097 mmol), 4-[(N-Boc)aminomethyl]aniline (222 mg, 1.0 mmol), HATU (418 mg, 1.10 mmol), DIPEA (350 µl), in DMF (20 ml) was stirred at room temperature for 4 hours. The solvent was removed under N2 flow, the residue was dissolved in 30 ml of ethyl acetate, the solution was washed successively with saturated aqueous solution of NaHCO₃ and saturated aqueous solution of NaCl and dried over anhydrous Na₂SO₄. After filtration the filtrate was evaporated in vacuo and the crude material was purified by flash chromatography (silica gel: 230-400 mesh; 2% methanol/DCM as eluent) to give the title compound. Yield: 395 mg (90%).

To the solution of 3 (380 mg, 0.86 mmol) in methanol (5 ml) of was added Pd/C (10%) 40 mg, hydrogen gas was bubbled for 8 h and TLC indicates complete disappear of starting material. After filtration the filtrate was evaporated under vacuum and the residue was triturated with ether repeatedly to 4 as colorless powder, yield: 240 mg (90%).

A mixture of 4 (240 mg, 0.78 mmol), Biotin (173 mg, 0.71 mmol), HATU (150 mg, 0.39 mmol), DIPEA (200 µl), in DMF (20 ml) was stirred at room temperature for 4 hours. The solvent was removed under N₂ flow, the residue was dissolved in 30 ml of ethyl acetate, the formed solution was washed successively with saturated aqueous solution of NaHCO₃ and saturated aqueous solution of NaCl and dried over anhydrous Na₂SO₄. After filtration the filtrate was evaporated under vacuum and the crude material was purified by flash chromatography (silica gel: 230-400 mesh; 10% methanol/DCM as eluent) to give 5. Yield: 145 mg (77%).

To a solution of 5 (140 mg, 0.26 mmol) in anhydrous DCM (5 ml) was add TFA (1 ml) at 0° C., and the temperature was increased slowly to room temperature, and then stirred for 2 h. The solvent and was removed under N₂ flow. The crude products were added to a solution of BocOrn(CbZ)OH (103 mg, 0.281 mmol), HATU (107 mg, 0.268 mmol), DIPEA (127 µl), in DMF (10 ml) was stirred at room temperature for 4 hours. The solvent was removed under N2 flow, the residue was dissolved in 30 ml of ethyl acetate, the formed solution was washed successively with saturated aqueous solution of NaHCO₃ and saturated aqueous solution of NaCl and dried over anhydrous Na₂SO₄. After filtration the filtrate was evaporated under vacuum and the crude material was purified by flash chromatography (silica gel: 230-400 mesh; 10% methanol/DCM as eluent) to give the title compound. Yield: 165 mg (90% in two steps).

To a solution of 6 (150 mg, 0.26 mmol) in anhydrous DCM (5 ml) was add TFA (1 ml) at 0° C., and the temperature was increased slowly to room temperature, and then stirred for 2 h. The solvent and was removed under N₂ flow. The crude products were used in the next step without purification.

A mixture of 7 (145 mg, 0.186 mmol), 6-(dimethylamino)-2-naphthoic acid (46 mg, 0.20 mmol), HATU (78 mg, 0.20 mmol), DIPEA (72 µl), in DMF (5 ml) was stirred at room temperature for 4 hours. The solvent was removed under N₂ flow, the residue was dissolved in 30 ml of ethyl acetate, the formed solution was washed successively with saturated aqueous solution of NaHCO₃ and saturated aqueous solution of NaCl and dried over anhydrous Na₂SO₄. After filtration the filtrate was evaporated in vacuo and the crude material was purified by flash chromatography (silica gel: 230-400 mesh; 5% methanol/DCM as eluent) to give 8. Yield: 139 mg (85%).

To the solution of 8 (135 mg, 0.153 mmol) in methanol (15 ml) of was added Pd/C (10%) 25 mg, hydrogen gas was bubbled for 8 h and TLC indicates complete disappear of starting material. After filtration the filtrate was evaporated under vacuum, the crude products were added to a solution of ethyl chloroacetamidate (46 mg, 0.380 mmol), TEA (150 up, in MeOH (4 ml) was stirred at room temperature for 24 hours. The solvent was evaporated in vacuo, the residue was dissolved in 20 ml of ethyl acetate, the formed solution was washed successively with saturated aqueous solution of NaHCO₃ (10 ml×3) and saturated aqueous solution of NaCl and dried over anhydrous Na₂SO₄. After filtration the filtrate was evaporated in vacuo and the crude material was purified by flash chromatography (silica gel: 230-400 mesh; 15% methanol/DCM as eluent) to give the title compound as pale yellow solid. Yield: 62 mg (50% in two steps).

The detailed scheme described for compound YW 4-15 can be used to synthesize other compounds of the present invention with minor routine modifications to achieve the desired compound.

Example 6

A representative synthesis of YW 1-30 is shown in synthetic Scheme 4.

Scheme 4:

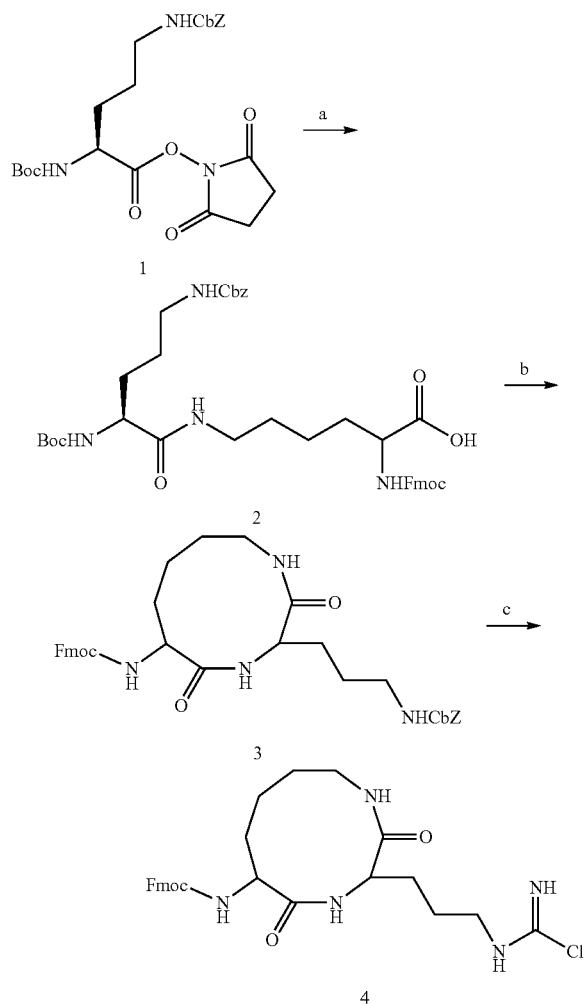

Reagents and Conditions:
a) Fmoc-Lys-OH, THF, H$_2$O, NaHCO$_3$, room temperature (rt), 12 hr, 62% yield.
b) 20% TFA in dichloromethane, rt, 2 hr; Bop, DIPEA, 69%
c) H$_2$, Pd/C, MeOH, rt; ethyl chloroacetamidate, MeOH, rt, 50% yield in two steps.

A mixture of BocOrn(CbZ)OSu (345 mg, 0.75 mmol), Fmoc-Lys-OH (298 mg, 0.80 mmol), NaHCO$_3$ (80 mg, 0.75 mmol) in THF (10 ml) and H$_2$O (2.5 ml) was stirred at room temperature for 12 hours. The solvent was evaporated in vacuo, the residue was purified by flash chromatography (silica gel: 230-400 mesh; 5% methanol/DCMe as eluent) to give the title compound as white solid. Yield: 332 mg (62%).

To a solution of 2 (332 mg, 0.44 mmol) in anhydrous DCM (10 ml) was add TFA (2 ml) at 0° C., and the temperature was increased slowly to room temperature, and then stirred for 2 h. The solvent and was removed under N$_2$ flow. The crude products were added to the solution of (Benzotriazol-1-yloxy)tris(dimethylamino)phosphonium hexafluorophosphate (213 mg, 0.484 mmol), DIPEA (75 µl) in THF (20 ml), the reaction mixture was stirred at room temperature for 12 hr. The solvent was evaporated in vacuo and the crude material was purified by flash chromatography (silica gel: 230-400 mesh; 5% methanol/DCM as eluent) to give the title compound, Yield: 182 mg (69% in two steps).

To the solution of 3 (200 mg, 0.43 mmol) in methanol (15 ml) of was added Pd/C (10%) 25 mg. The reaction mixture was stirred under H$_2$ balloon at rt for 8 hours. After filtration the filtrate was evaporated in vacuo, the crude products were added to a solution of ethyl chloroacetamidate (200 mg, 0.86 mmol), TEA (52 µl), in MeOH (4 ml) was stirred at rt for 4 hours. The solvent was evaporated in vacuo, the residue was dissolved in 20 ml of ethyl acetate, the formed solution was washed successively with saturated aqueous solution of NaHCO$_3$ (10 ml×3) and saturated aqueous solution of NaCl and dried over anhydrous Na$_2$SO$_4$. After filtration the filtrate was evaporated in vacuo and the crude material was purified by flash chromatography (silica gel: 230-400 mesh; 15% methanol/DCM as eluent) to give the title compound as pale yellow solid. Yield: 95 mg (41% in two steps).

The detailed scheme described for compound YW 1-30 can be used to synthesize other compounds of the present invention with minor routine modifications to achieve the desired compound.

Example 7

MIT assays are conducted to evaluate activity to inhibit cancer cell growth. U2OS human osteosarcoma cells were treated with individual compounds at different concentrations for 72 hr in 24-well plates. MIT reagent was added to a final concentration of 0.5 mg/ml and further incubated for 4 hr. The yellow-colored MTT was reduced to insoluble purple-colored Formazan in living cells. Culture medium was removed and DMSO was added to dissolve Formazan into solution. The absorbance of the solution was then measured at 570 nm using a Thermo BioMate™ 3 spectrophotometer. Results are shown in FIG. 1 and average and standard deviations are shown (n>=3).

Example 8

PAD4 enzyme activity assays are conducted to determine PAD4 inhibitory activity. PAD4 inhibition efficacy of the inhibitors is determined using a colorimetric assay for citrullination production.

The inhibition efficacy of PAD4 inhibitors were determined by colorimetric measurement of citrulline generated by PAD4 catalyzed citrullination of BAEE. 0.2 µg PAD4 was pre-incubated with inhibitors in 100 µl buffer containing 50 mM Tris-HCl pH7.6, 5 mM CaCl$_2$, 2 mM DTT for 0.5 hr at 37° C. The reaction was started by the addition of BAEE to 5 mM and halted 1.5 hr later with the addition of 25 µl 5 M HClO$_4$. Then the samples were briefly centrifuged at 12000 rpm for 2 min at 4° C. and the supernatant (120 µl) were assayed for citrulline by mixing with 120 µl reagent A (0.5% w/v diacetyl monoxime and 15% w/v NaCl in water) and 240 µl reagent B (1% w/v antipyrine, 0.15% w/v ferric chloride, 25% v/v H$_2$SO$_4$ and 25% v/v H$_3$PO$_4$). The mixtures were boiled for 15 min and cooled to room temperature in ice bath. The absorbance of the reagent mixtures at 464 nm was measured by Thermo BioMate™ 3 spectrophotometer. Efficacies of inhibitors are indicated as relative PAD4 citrullination activity by normalizing the PAD4 activity without inhibitor treatment to 100%.

Figure 2:
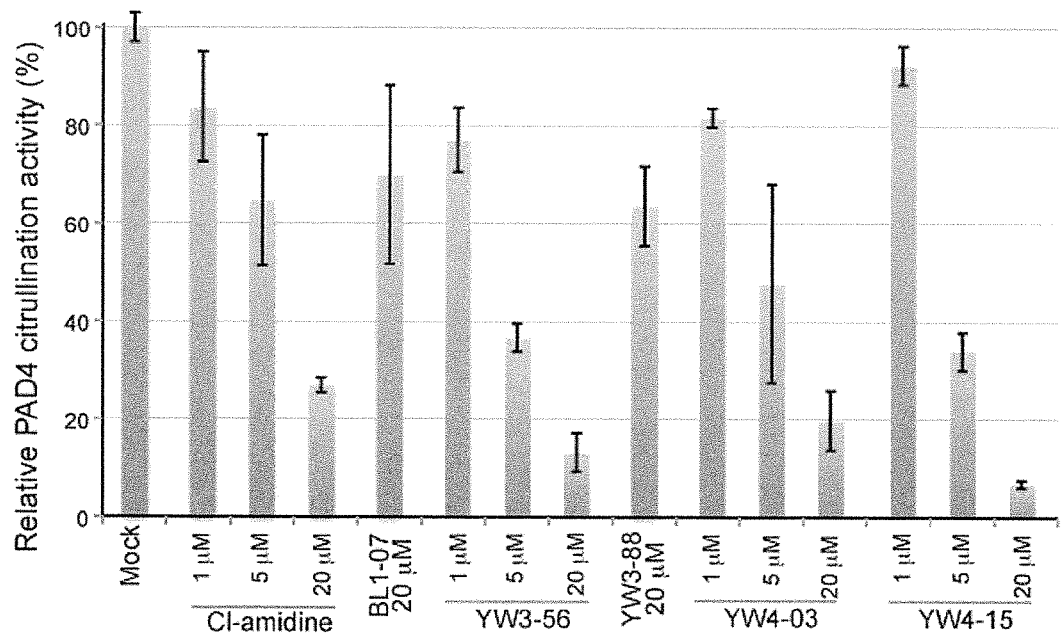
FIG. 2 is a graph showing results of PAD4 enzyme activity assays conducted to PAD4 inhibition efficacy of compounds.

Results are shown in FIG. 2 and average and standard deviations are shown (n>=3). Results in FIG. 2 are representative of PAD4 inhibitory activity of compounds described herein and similar results are obtained identifying the compounds described herein as PAD4 inhibitors.

$IC_{50}$ values (μM) to inhibit cancer cell growth and $IC_{50}$ values (μM) to inhibit PAD4 activity are shown for several compounds in Table I.

TABLE I

| 50% inhibition | Cell growth (μM) | PAD4 activity (μM) |
|---|---|---|
| CI-amidine | 150-200 | 5-20 |
| YW3-56 | ~2.5 | 1-5 |
| YW3-88 | ~10 | >20 |
| YW4-03 | 2.5-5 | ~5 |
| YW4-15 | 20-50 | 1-5 |
| BL1-07 | 10-20 | >20 |

Example 9

Figure 3:
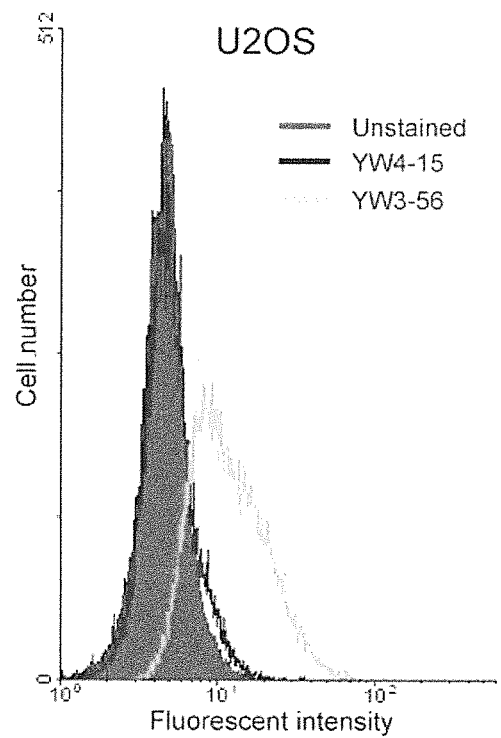
FIG. 3 is a graph showing results of flow cytometry analysis of uptake of compounds YW3-56 and YW4-15.

Compounds YW3-56 and YW4-15 are evaluated using flow cytometry to assess cellular uptake. U2OS cells treated with 10 μM of YW3-56 or YW4-15 for 12 hr were harvested and washed with PBS once. Cell pellet was resuspended in 1 ml of pre-warmed DMEM. The untreated cells were used as negative control. The fluorescence was assessed by FC500 flow cytometer (Beckman Coulter Inc.) and analyzed with WinMDI 2.9 software. Results are shown in FIG. 3.

Example 10

Cell Growth Inhibition Effects of PAD4 Inhibitors Analyzed by MTT Assays

Cells were treated with individual compounds at different concentrations for 72 hr in 24-well plates. MTT reagent was added to a final concentration of 0.5 mg/ml and further incubated for 4 hr. The yellow-colored MTT was reduced to insoluble purple-colored Formazan in living cells. Culture medium was removed and DMSO was added to dissolve Formazan into solution. The absorbance of the solution was then measured at 570 nm using a Thermo BioMate™ 3 spectrophotometer.

Figure 4A:
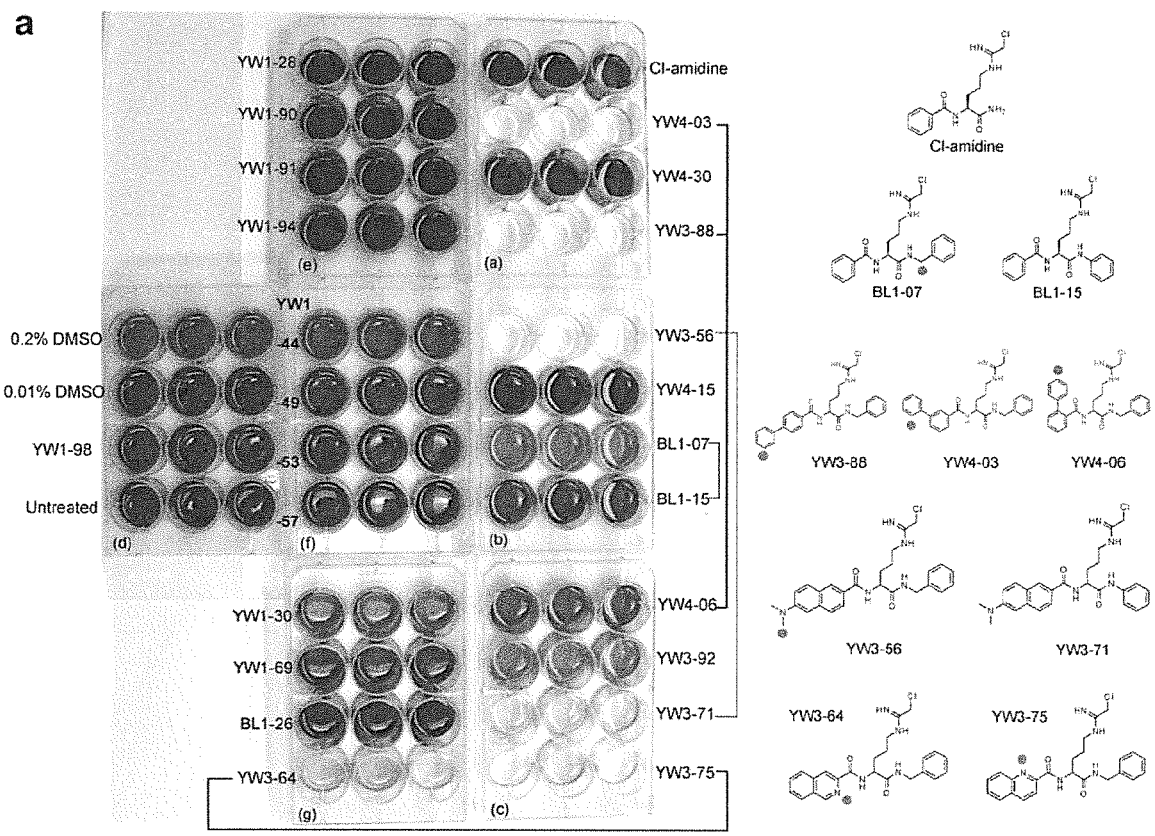
FIG. 4A is an image showing results of MTT assays conducted to evaluate activity of compounds to inhibit cancer cell growth.

FIG. 4A shows representative images illustrating the effects of PAD4 inhibitors of the present invention on U2OS cell growth inhibition using MTT assays with all inhibitors used at 20 μM concentration for 3 days. Several inhibitors, YW4-03, YW3-88, and YW3-56 abolished cell growth at 20 μM concentration. Compounds with similar structures are grouped and structural differences denoted by dots.

Figure 4B:
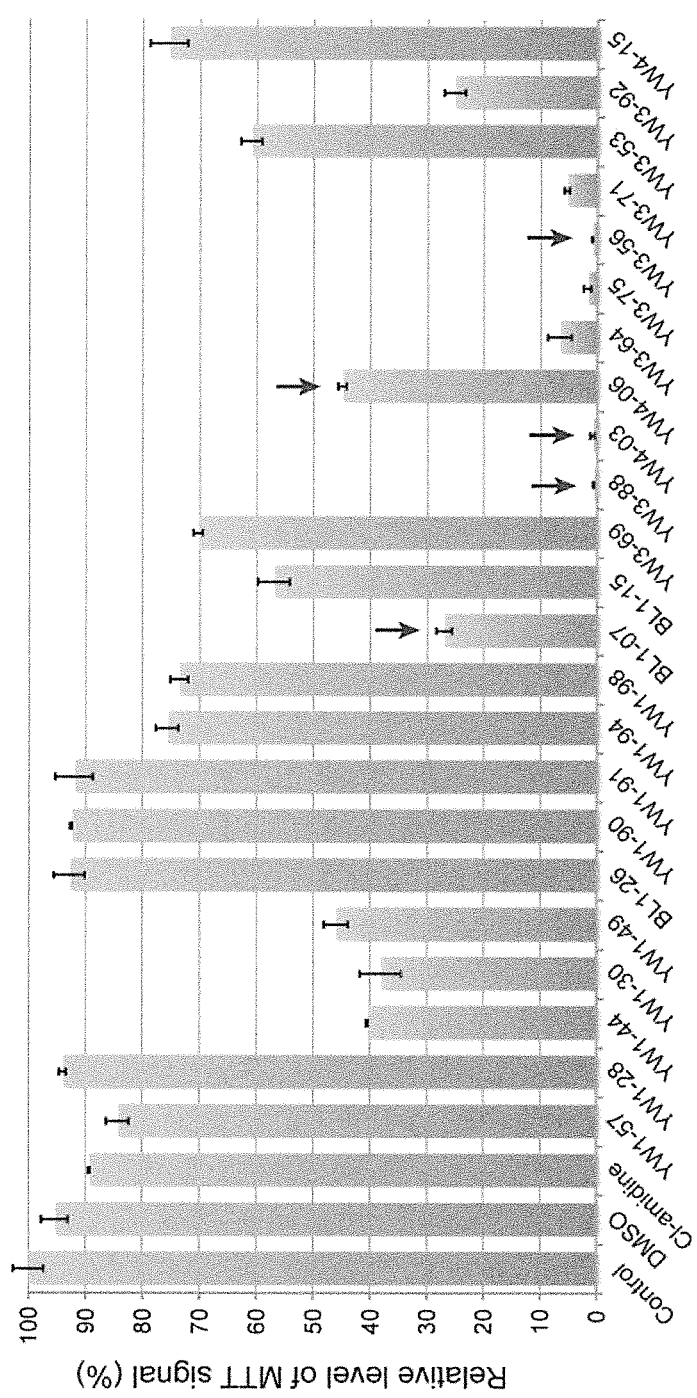
FIG. 4B is a graph showing results of MTT assays conducted to evaluate activity of compounds to inhibit cancer cell growth.

FIG. 4B shows MTT signals measured as an absorbance value at 570 nm wavelength after U2OS cells are treated with various PAD4 inhibitors at 20 μM concentration. Averages and standard deviations are shown (n=3).

Example 11

Cell growth and morphology changes of cells treated with compounds of the present invention are analyzed using phase contrast microscopy.

A VistaVision invert microscope (VWR Inc.) equipped with a Spot Insight digital camera (NDS, Inc.) and a 10× phase contrast lens were used to analyze cell growth and morphology in phase contrast microscopy analyses.

Figure 5:
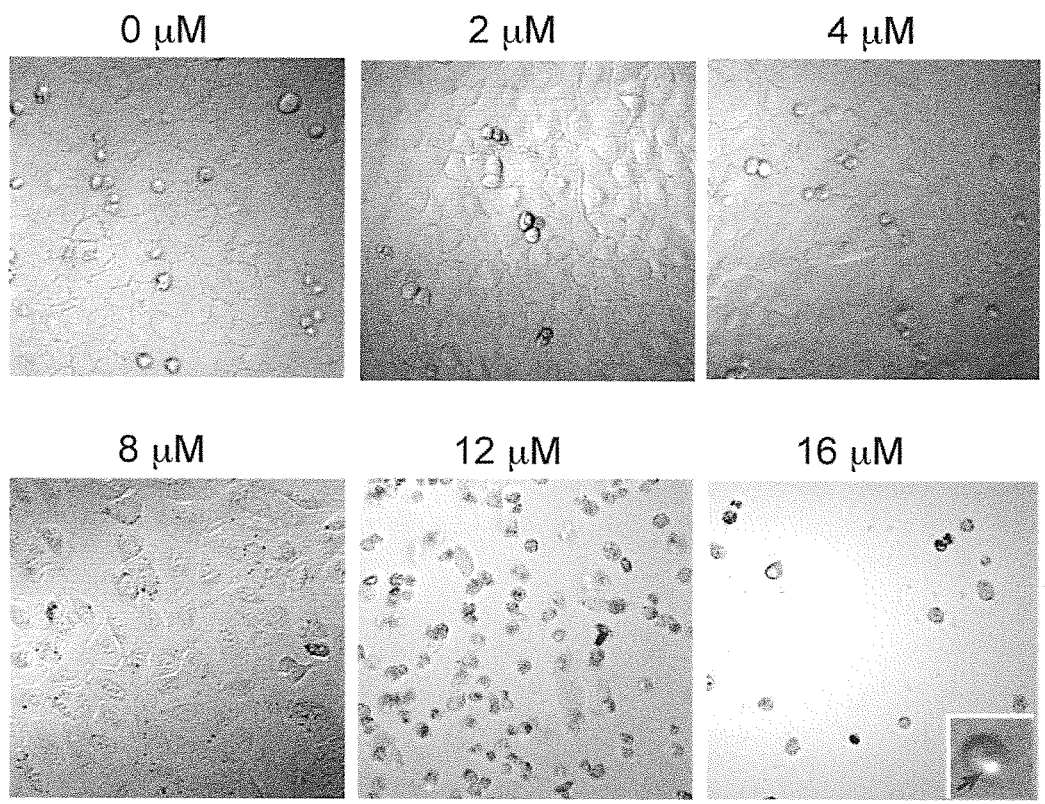
FIG. 5 is a series of images showing effects of various concentrations of PAD4 inhibitor YW3-56 on U2OS cancer cells.

In this example, U2OS are treated with 0, 2, 4, 8, 12 or 16 μm YW3-56 for 24 hours. YW3-56 treatment decreases U2OS cell density in culture in a concentration-dependent manner as shown in FIG. 5.

Cells gradually lose their attachment to culture dishes and floated when 8-16 μM of YW3-56 is applied. Prominent characteristics of apoptotic cells, such as chromatin condensation and fragmentation, are not detected in U2OS cells after YW3-56 treatment. Unexpectedly, large clear bubbles are observed in most YW3-56 treated cells, exemplified in the inset to FIG. 5. Compounds of the present invention are effective in preventing the growth of other types of cancer cells in addition to the U2OS cells, including breast cancer cells, colon cancer cells, and others.

Example 12

Figure 6:
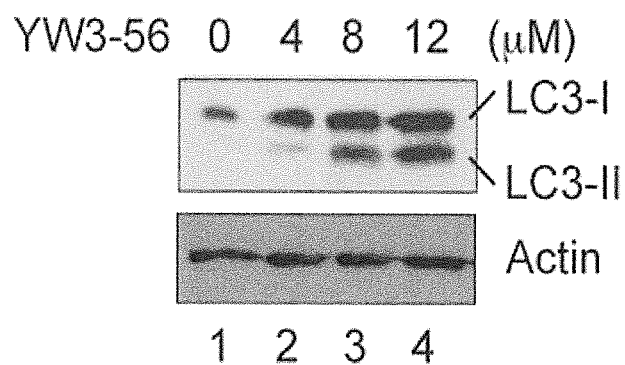
FIG. 6 is an image of a Western blot showing effects of PAD4 inhibitor YW3-56 on cleavage of LC3-I, indicative of cell death.

YW3-56 induces cell death by autophagy, a cell death process in which cellular proteins and organelles are degraded by fusion with lysosomes. Cleavage of LC3-I to generate a fast migrating isoform LC3-II is a characteristic autophagy event. LC3 cleavage is induced after YW3-56 treatment in a concentration-dependent manner as shown in the Western blot in FIG. 6.

Western blot and immunostaining was performed essentially as described in Li, P. et al., Oncogene 29 (21), 3153-3162 (2010). Antibodies used in Western blot were anti-p53 (Sigma), anti-PAD4, anti-p21 (Sigma), anti-PUMA (Calbiochem), anti-SESN2 (Abeam), anti-p70S6K (Cell Signaling), anti-p70S6K-pT389 (Cell Signaling), anti-LC3 (Cell Signaling) and anti-β-actin (Sigma) at appropriate dilutions. Anti-LC3B antibody (Cell Signaling) was used for immunostaining. DNA was stained by the DNA dye Hoechst.

Figure 7:
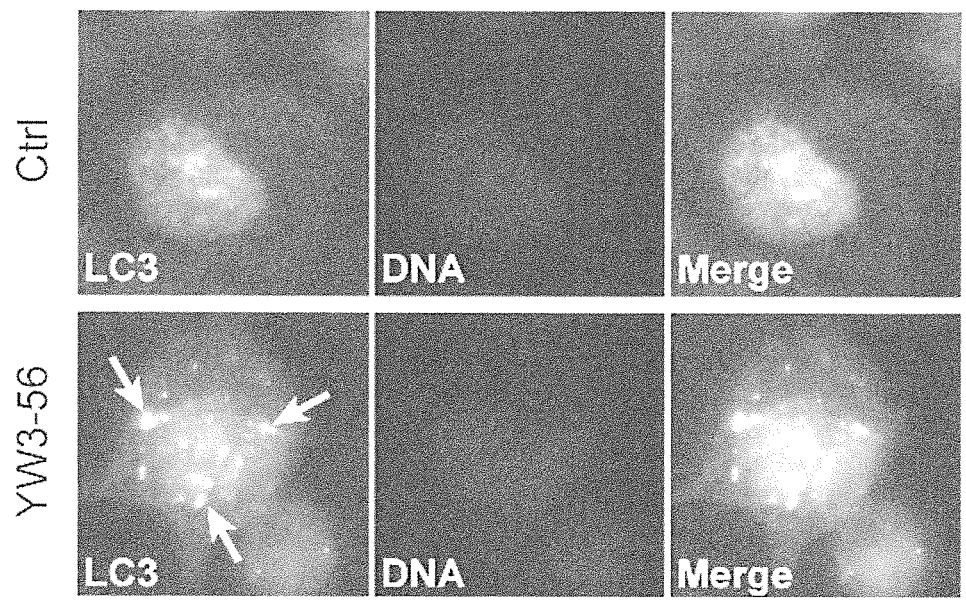
FIG. 7 is an image showing LC3 staining in U2OS cancer cells treated with PAD4 inhibitor YW3-56.

LC3 staining is detected in multiple large speckles in U2OS cells after YW3-56 treatment but not in control cells, suggesting the formation of autophagosomes and autophagolysosomes after YW3-56 treatment as shown in FIG. 7.

Figure 8:
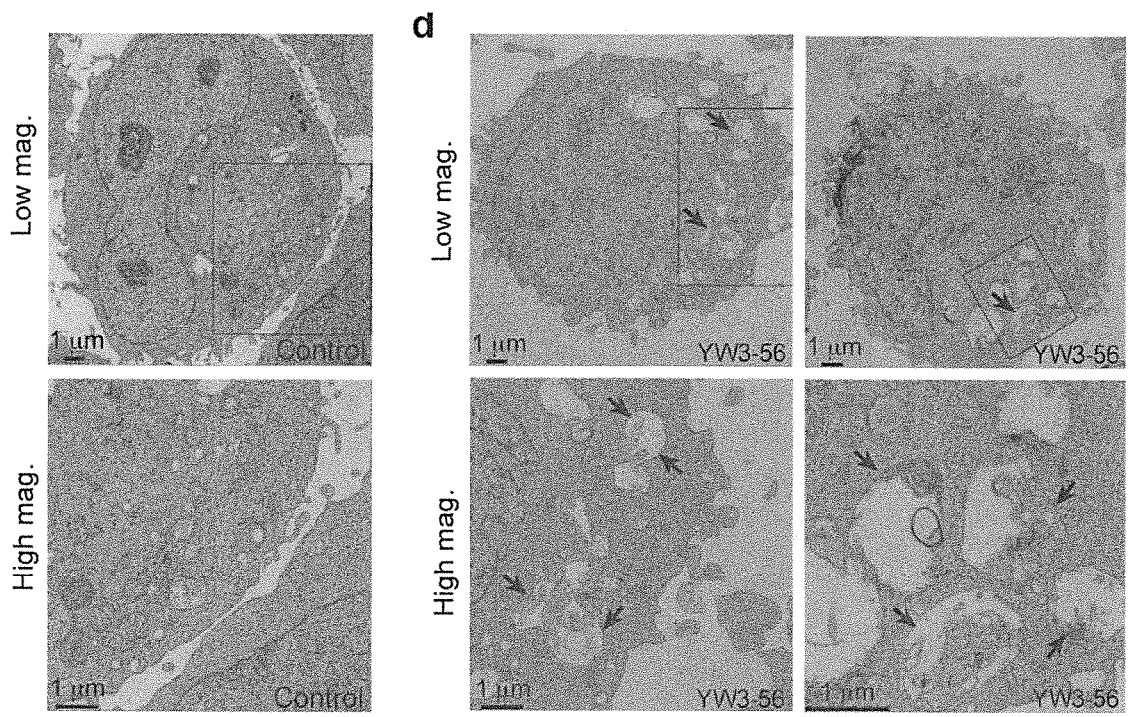
FIG. 8 is a series of transmission electron micrographs showing vesicles having structural characteristics of autophagosomes and autophagolysosomes in YW3-56 treated cells but not in control cells.

U2OS Cells were treated with 6 μM YW3-56 for 24 hr, fixed in 2% glutaraldehyde in 0.1 M phosphate buffer, pH7.4. Transmission electron microscopy analyses of U2OS cells morphology were performed using the service of the Penn State Electron Microscopy Facility. Transmission electron microscopy analyses are performed and multiple large vesicles containing engulfed membrane- and organelle-structures, with structural characteristics of autophagosomes and autophagolysosomes, are detected in YW3-56 treated cells but not in control cells as shown in FIG. 8.

Distinctive structures with characteristics of autophagosomes or autophagolysosomes are detected in YW3-56 treated cells (denoted by arrows). Two representative cells are shown at low and high magnification.

Example 13

PAD4 Inhibitors Inhibit Cancer Growth In Vivo

A well-established sarcoma S180 cell-derived mouse tumor model is used in this example to determine the effects of PAD4 inhibitors of the present invention on tumor growth in mice.

S180 ascites tumor cells were used to form solid tumors after subcutaneous injection essentially as described in Wang, W. et al., Mol. Biosyst., 2011, 7:766-772. In brief, for initiation of subcutaneous tumors, the cells were obtained as an ascitic form from the tumor-bearing mice, which were serially transplanted once per week. Subcutaneous tumors were implanted by injecting 0.2 ml of 0.9% saline containing 1×10[7] viable tumor cells under the skin on the right armpit. 24 hr after implantation, male ICR mice were randomly divided into experimental groups. The mice in the positive control group were given a daily i.p injection of 2 mg/kg of doxorubicin in 0.2 ml of 0.9% saline for 7 consecutive days. The mice in the negative control group were given a daily i.p injection of 0.2 ml of 0.9% saline for 7 consecutive days. The mice in the treatment groups were given a daily i.p injection of YW3-56 (10 mg/kg), SAHA (5 mg/kg), or a combination of YW3-56 (5 mg/kg) and SAHA (2.5 mg/kg) for 7 consecutive days. The weights of the mice were recorded every day. 24 hr after the last administration, all mice were weighed, euthanized and immediately dissected to obtain and weigh the tumor and vital organs.

Figure 9:
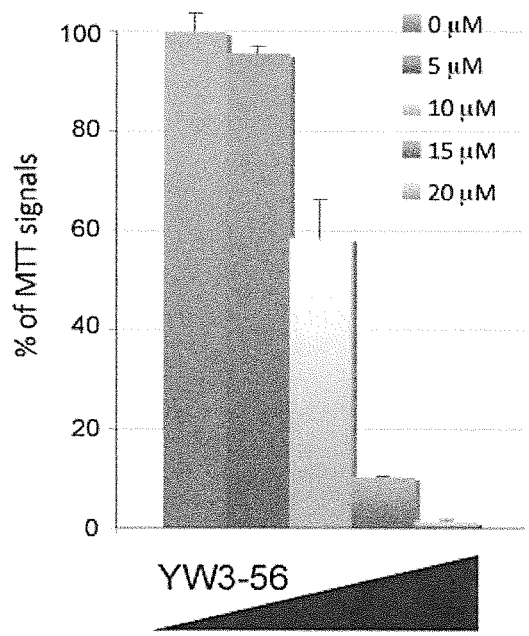
FIG. 9 is a graph showing characteristics of inhibition of S180 sarcoma tumors.

The growth inhibition $IC_{50}$ of YW3-56 in S180 cells is ~10-15 µM in MTT assays as shown in FIG. 9.

Figure 10:
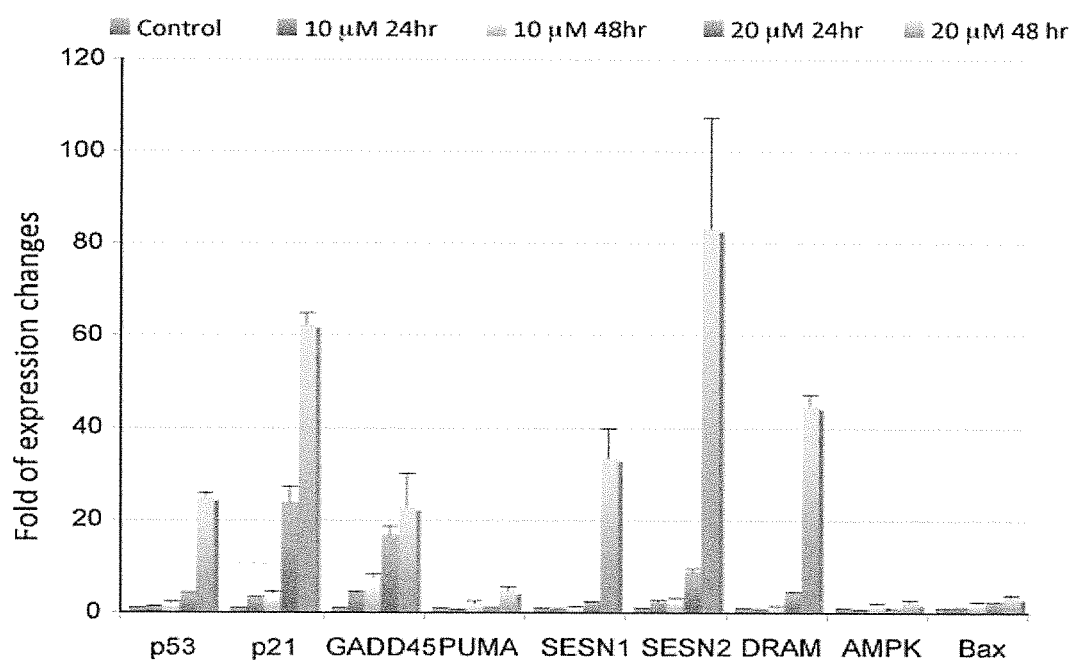
FIG. 10 is a graph showing p53 and its target gene expression induced in S180 cells by YW3-56 in a concentration dependent manner.

RT-qPCR analyses confirmed that YW3-56 treatment induced the expression of p53 and its target genes, including sestrin1 (SESN1) and sestrin2 (SESN2), in a concentration dependent manner. RNA was extracted using RNeasy Mini Kit (Qiagen) per manufacturer's instructions. 1 µg RNA was reverse transcribed into cDNA using qScript cDNA Super-Mix (Quanta Biosciences) per manufacturer's instructions. Quantitative PCR was performed using SYBR Green Super-Mix (Quanta Biosciences) in StepOnePlus Real-Time PCR System (Applied Biosystems). FIG. 10 is a graph showing p53 and its target gene expression induced in S180 cells by YW3-56 in a concentration dependent manner.

Expression of p53 and its target genes in mouse liver and spleen after YW3-56 injection at 10 mg/kg body weight once every two days for 3 months.

Figure 11A:
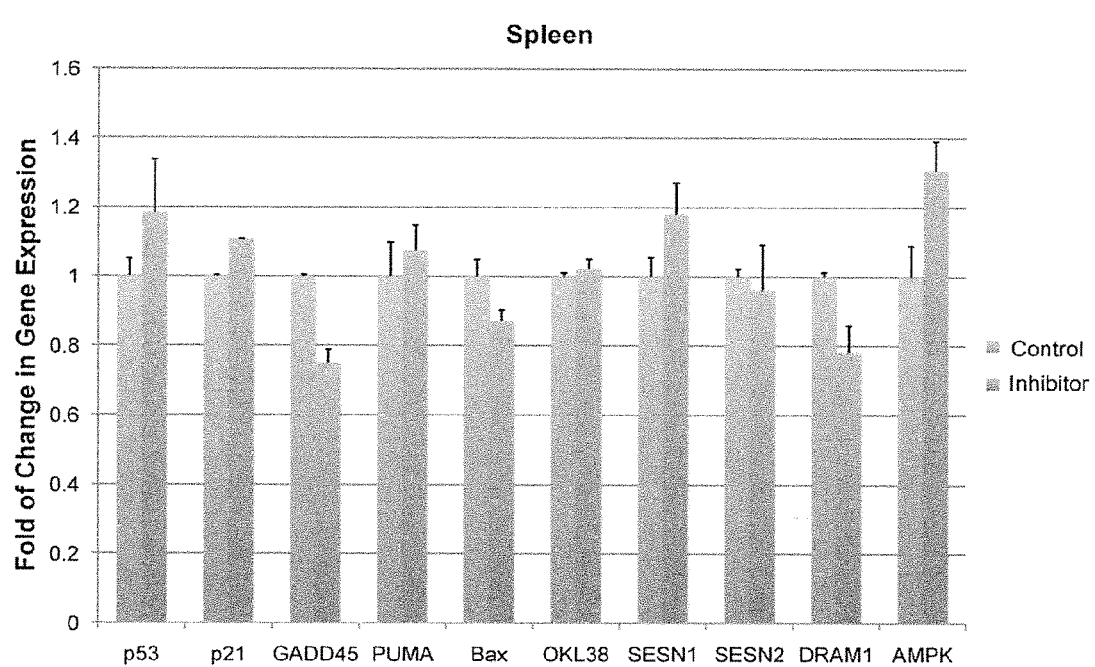
FIG. 11A is a graph showing results of RT-qPCR analyses of p53 and its target gene mRNA levels in spleen of control and YW3-56 treated mice.
Figure 11B:
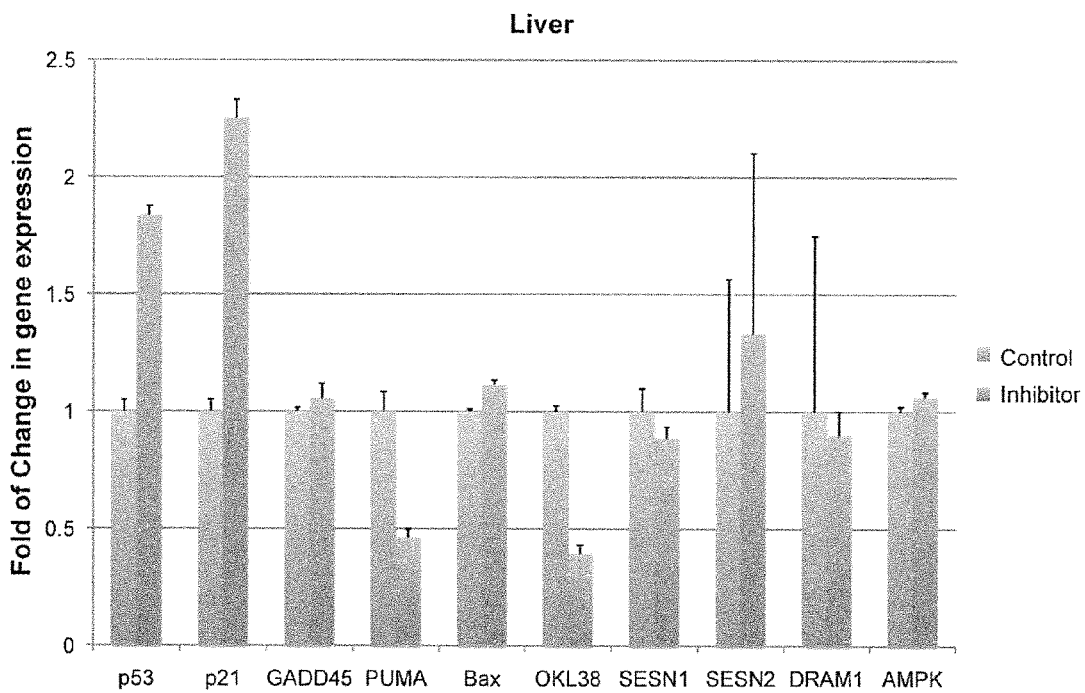
FIG. 11B is a graph showing results of RT-qPCR analyses of p53 and its target gene mRNA levels in liver of control and YW3-56 treated mice.

FIGS. 11a and 11b show results of the effect of long term YW3-56 treatment in mice. A pair of nude mice is mock injected or injected with YW3-56 for three months. RT-qPCR analyses of p53 and its target gene mRNA levels in control and YW3-56 treated mice. Changes in gene expression in spleen are not detected if 2-fold expression change is used as a cut off as shown in FIG. 11a. FIG. 11b shows results of RT-qPCR analyses of p53 and its target gene expression in livers of treated and mock treated mice. ~2 fold increase in p53 and p21 mRNA is detected, while ~2-fold decrease in PUMA and OKL38 is detected in liver samples, suggesting some changes in gene expression in liver after YW3-56 treatment. However, these changes are at low levels and no clear change in liver weight and morphology is observed.

Figure 12:
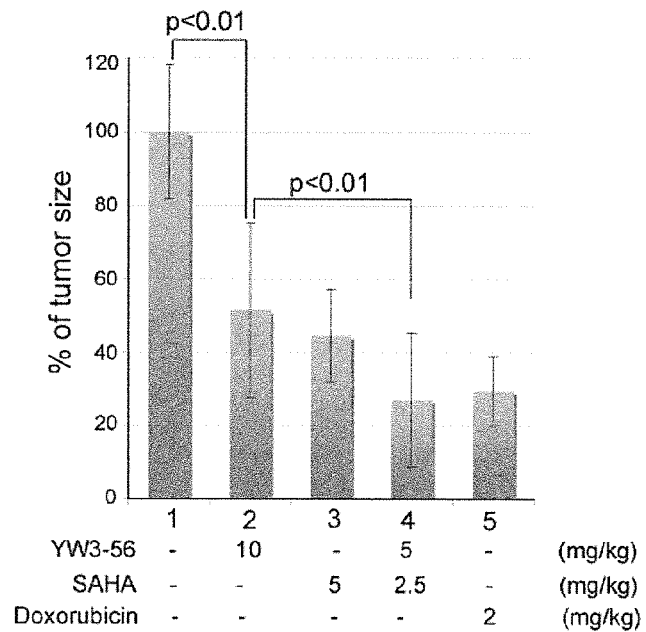
FIG. 12 is a graph showing the effects of the PAD4 inhibitor, YW3-56, on tumors in mice.

Upon intraperitoneal injection of YW3-56 at a concentration of 10 mg/kg mouse body weight daily for 1 week, the growth of S180 tumor is decreased to ~51.5% of that of the control group injected with a isotonic saline solution as shown in FIG. 12.

SAHA (also called Vorinostat) is a US FDA approved drug for treatment of cutaneous T cell lymphoma by inhibiting HDACs to elevate histone acetylation and increase tumor suppressor gene expression. As a reference to compare and evaluate the effect of YW3-56, the HDAC inhibitor SAHA is injected at 5 mg/kg body weight concentration daily for 1 week. S180-derived tumor growth in these mice decreased to ~44.6% of that of the control group as shown in FIG. 12.

Since PAD4 coordinates with HDAC2 in repressing p53-target gene expression, the synergy of PAD4 inhibitor and HDAC inhibitor in tumor growth is tested in this example. Following injection of a mix of YW3-56 and SAHA at half of their concentrations when applied singularly, tumor growth is decreased to ~27.1% of that of the control group, shown in FIG. 12, suggesting synergistic effects of these inhibitors. In comparison to doxorubicin, a well-established chemotherapeutic reagent, a mixture of YW3-56 and SAHA shows cancer growth inhibition effect close to that of doxorubicin applied at 2 mg/kg body weight concentration, shown in FIG. 12.

Weight of body weight and vital organs in mice without or with YW3-56, SAHA, YW3-56 and SAHA, or doxorubicin treatment.

Figure 13A:
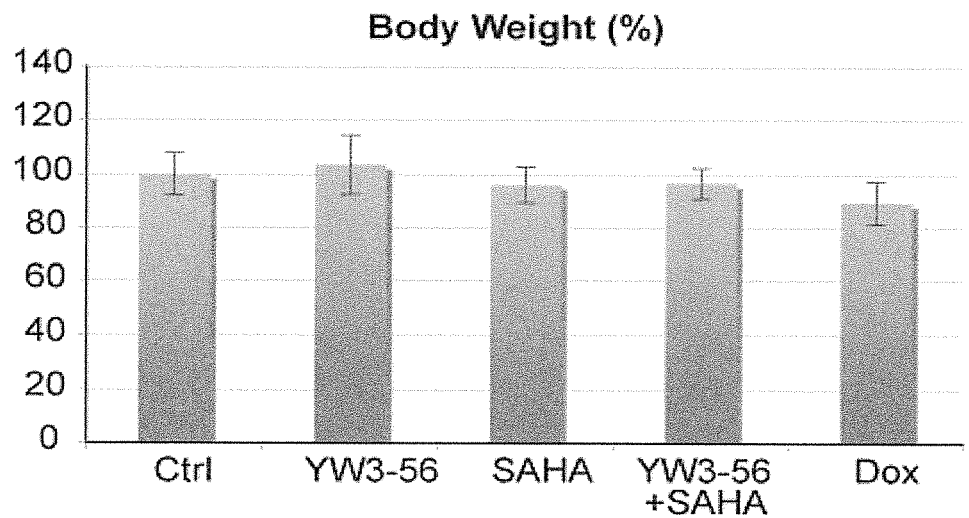
FIG. 13A is a graph showing whole body weight of mice after treatment with the indicated agent.
Figure 13B:
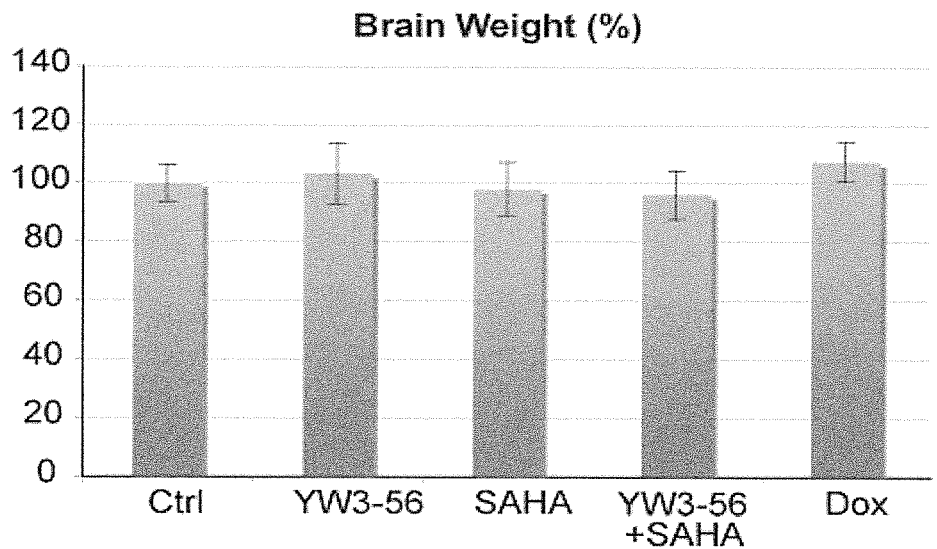
FIG. 13B is a graph showing brain weight of mice after treatment with the indicated agent.
Figure 13C:
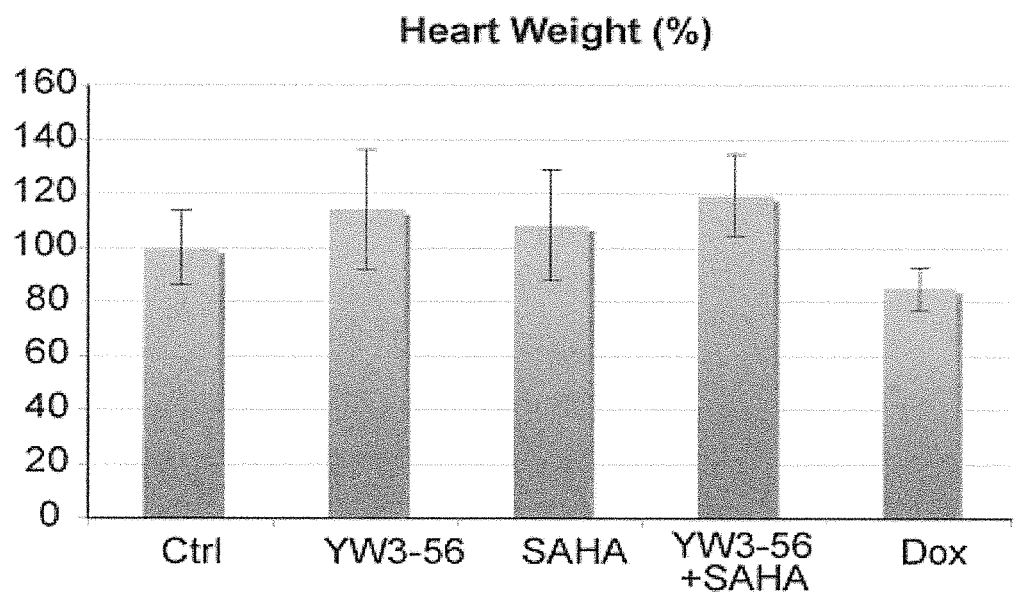
FIG. 13C is a graph showing heart weight of mice after treatment with the indicated agent.
Figure 13D:
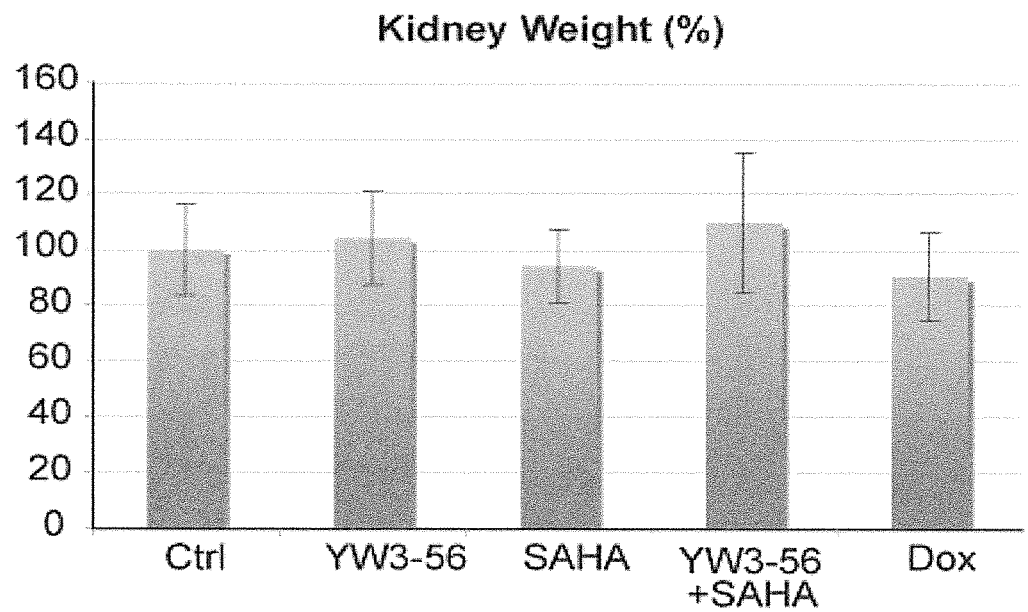
FIG. 13D is a graph showing kidney weight of mice after treatment with the indicated agent.
Figure 13E:
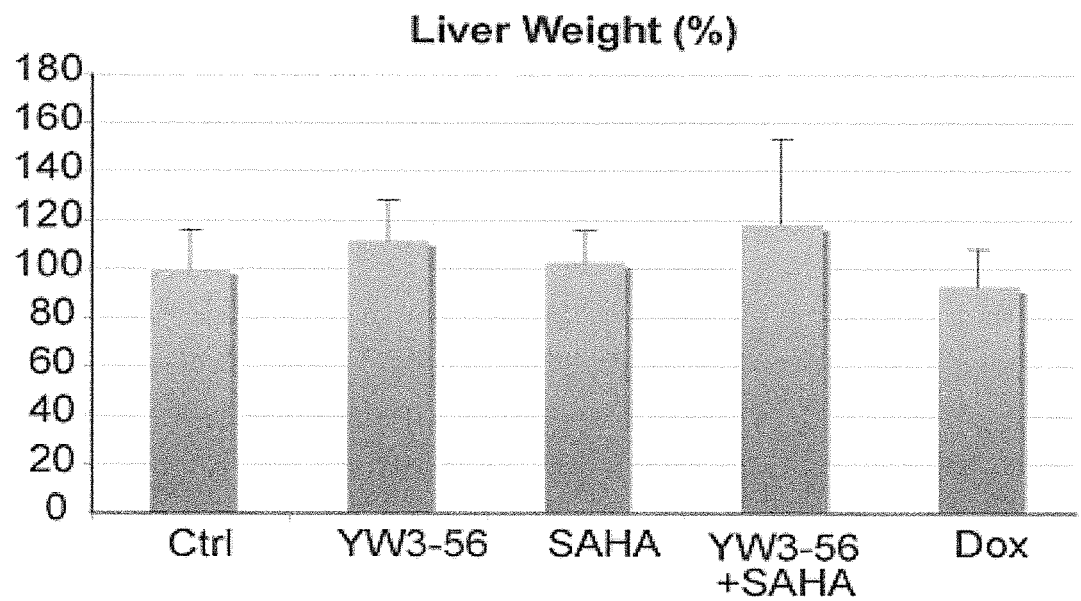
FIG. 13E is a graph showing liver weight of mice after treatment with the indicated agent.
Figure 13F:
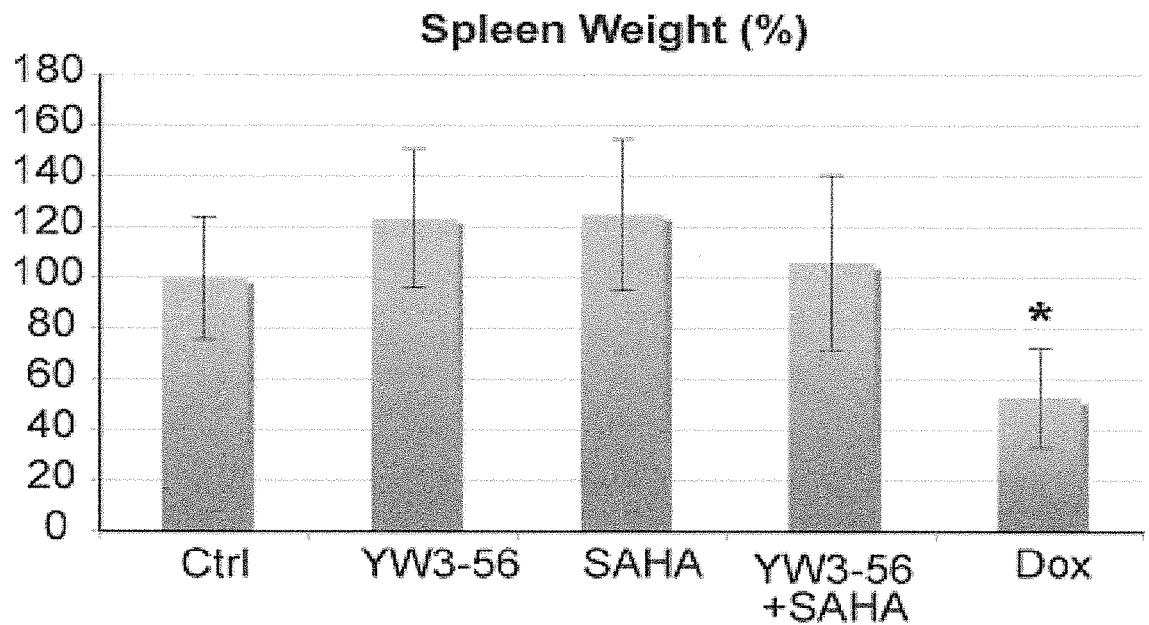
FIG. 13F is a graph showing spleen weight of mice after treatment with the indicated agent.

FIG. 13A-13F show weight of whole body, FIG. 13A; brain, FIG. 13B; heart, FIG. 13C; liver, FIG. 13D; kidney, FIG. 13E; and spleen, FIG. 13F measured in mice after 1 week of treatment with daily intraperitoneal injection of control PBS, YW3-56 at 10 mg/kg body weight, SAHA at 5 mg/kg body weight, a mixture of YW3-56 at 5 mg/kg body weight and SAHA at 2.5 mg/kg body weight, or doxorubicin at 2 mg/kg body weight. * in (f) denotes a loss of spleen weight after doxorubicin treatment.

Neither SAHA alone nor mixtures of YW3-56 and SAHA impair mouse growth and vital organ size as shown in FIGS. 13B-13F. In contrast, the size of spleen is decreased to ~50% of that of control mice after doxorubicin treatment, shown in FIGS. 13A-13F, suggesting that inhibitors targeting epigenetic pathways are less toxic compared with inhibitors that directly inhibit cell cycle.

A three-month YW3-56 treatment including daily injection of YW3-56 at 10 mg/kg body weight in a pair of nude mice is performed and the size of mouse body and vital organs is not altered after YW3-56 treatment as shown in FIG. 13. Moreover, with the exception of a slight increase in p53 and p21 mRNA in liver, levels of p53 and its target genes are not much altered after YW3-56 treatment in liver and spleen tissues, indicating that YW3-56 does not drastically affect gene expression in normal tissues and organs in mice.

Example 14

PAD4 is involved in the releasing of chromatin into extracellular space to form chromatin NETs (neutrophil extracellular traps).

NET formation is induced after lipopolysaccharides (LPS) and phorbol myristate acetate (PMA) treatment in human neutrophils (Brinkmann et al., 2004). To test whether PAD4 is important for chromatin decondensation and NET formation upon LPS treatment, immunostaining experiments are performed. Before LPS treatment, ~3.69% of PAD4[+/+] neutrophils are positively stained for histone H3 citrullination but NET formation is not detected, while histone H3 citrullination or NET formation is not observed in PAD4[-/-] neutrophils. After LPS treatment, an increase in histone H3 citrullination is detected in PAD4[+/+] but not in PAD4[-/-] neutrophils by Western blotting or immunostaining analyses. DNA staining identified chromatin decondensation to various degrees after LPS treatment, including swelling nuclei (nuclear area quantification with the NIH image J program shows about ~3.5 fold increase in size) and elongated chromatin in PAD4[+/+] neutrophils. The decondensed chromatin induced by LPS is positively stained by histone H3 citrullination and neutrophil elastase antibodies, indicating these structures are indeed NETs. The PAD inhibitor Cl-amidine represses the formation of NET-like structure in human HL-60 granulocytic cells (Wang et al., 2009). Similarly, pretreatment of PAD4[+/+] mouse neutrophils with Cl-amidine significantly decreases histone H3 citrullination and chromatin decondensation induced by LPS, suggesting that PAD activity is important for NET formation. Furthermore, chromatin decondensation and histone citrullination are detected in PAD4[+/+] but not in PAD4[-/-] neutrophils after PMA treatment. These results indicate PAD4$^{-/-}$ mouse neutrophils lack the ability to citrullinate histones or form NETs after LPS and PMA treatment.

Reactive oxygen species (ROS), such as $H_2O_2$, induce the formation of NETs in adult neutrophils (Fuchs et al., 2007; Neeli et al., 2008) but not in newborn infant neutrophils (Yost et al., 2009), suggesting that the cellular responses downstream of ROS are important in regulating NET formation.

To test if $H_2O_2$ induced NET formation requires PAD4, PAD4$^{+/+}$ and PAD4$^{-/-}$ neutrophils are treated with $H_2O_2$. Histone H3 citrullination and NET formation are detected in PAD4$^{+/+}$ but not in PAD4$^{-/-}$ neutrophils after $H_2O_2$ treatment, indicating that PAD4 functions downstream of $H_2O_2$ stimulus during NET formation.

Table II illustrates the efficacy of LPS, PMA, and $H_2O_2$ in inducing chromatin structure changes in PAD4$^{+/+}$ and PAD4$^{-/-}$ neutrophils. Table II shows percentages of mouse neutrophils with positive histone citrullination, enlarged nucleus and NET formation after treatment with LPS, PMA and $H_2O_2$. PAD4 is required for NET formation after stimulation of neutrophils.

TABLE II

Percentages of mouse neutrophils with positive histonecitrullination, enlarged nucleus, and NET formation after treatment with LPS, PMA, and $H_2O_2$.

| | PAD4$^{+/+}$ | | | PAD4$^{-/-}$ | | |
|---|---|---|---|---|---|---|
| | Histone citrullination | Enlarged nucleus[1,2] | NET formation[3,4] | Histone citrullination | Enlarged nucleus | NET formation |
| Control | 3.7 ± 0.3%[5] | U.D.[6] | U.D. | U.D. | U.D. | U.D. |
| LPS | 42.3 ± 3.9%[5] | 23.4 ± 2.7%[5] | 9.5 ± 0.5%[5] | U.D. | U.D. | U.D. |
| Cl-amidine[7]→LPS | 8.1 ± 1.3%[5] | 1.2 ± 0.2%[5] | 0.32 ± 0.3%[5] | U.D. | U.D. | U.D. |
| PMA | 48.5 ± 3%[5] | 10.9 ± 0.3%[5] | 2.7 ± 0.5%[5] | U.D. | U.D. | U.D. |
| $H_2O_2$ | 48.3 ± 5.4%[5] | 13.4 ± 1.4%[5] | 3 ± 0.3%[5] | U.D. | U.D. | U.D. |

[1]Nucleus is scored as an enlarged nucleus if its nuclear diameter is over 1.5 fold larger than a regular neutrophil, which is ~10 μm in diameter.
[2]Enlarged nuclei were found to be histonecitrullination positive.
[3]NET formation is scored if chromatin has extruded and elongated from the nucleus to extracellular space and is confirmed by neutrophilelastase staining after LPS treatment.
[4]NETs were found to be histonecitrullination positive.
[5]Averages and standard deviations were shown (three independent experiments, over 500 cells were counted from each experiment).
[6]U.D., undetectable.
[7]200 μM Cl-amidine was used to treat neutrophils for 30 min prior to LPS treatment for 3 hr.

Histone citrullination and nuclear morphology in untreated neutrophils. A small number (~3.69%) of PAD4$^{+/+}$ neutrophils show robust histone H3 citrullination (H3Cit) staining before treatment with various stimulating compounds. Decondensed chromatin is not observed before stimulation. In contrast, histone H3Cit or chromatin decondensation is not observed in PAD4$^{-/-}$ neutrophils. Neutrophils are purified from 5 mice per genotype in three independent repeat experiments. LPS treatment induces histone citrullination and chromatin structural changes in PAD4$^{+/+}$ neutrophils. Swelling nuclei and chromatin elongation is observed. In contrast, LPS treatment does not induce histone citrullination or chromatin structural changes in PAD4$^{-/-}$ neutrophils. Histone citrullination and neutrophil elastase staining co-localize with decondensed chromatin in PAD4$^{+/+}$ neutrophils after LPS treatment. $H_2O_2$ treatment induces histone citrullination and chromatin structural changes in PAD4$^{+/+}$ neutrophils but not in PAD4$^{-/-}$ neutrophils. Peripheral blood neutrophils are purified from 5 PAD4$^{+/+}$ or 5 PAD4$^{-/-}$ mice each time in three independent experiments for LPS, and $H_2O_2$ treatment, respectively.

Although each of the treatments elicits nuclear morphology changes and NET formation to certain extent, LPS is the most potent inducer for NET formation under current treatment conditions. Furthermore, reverse transcription PCR (RT-PCR) experiments show that the depletion of PAD4 in neutrophils does not affect the expression of other PAD family members that encode active enzymes, including PAD-1, -2, and -3. Taken together, above results indicate that PAD4 is important for NET formation in mouse neutrophils upon treatment with proinflammatory stimuli, such as LPS, PMA, and $H_2O_2$.

Example 15

PAD4 inhibitors activate tumor suppressor gene expression and induce autophagy via inhibition of the mTOR signaling pathway.

MTT assays are performed in U2OS cells with or without p53 depletion to analyze the role of p53 in YW3-56 mediated cell growth inhibition and autophagy.

U2OS and S-180 cells were cultured in Dulbecco modified Eagle medium (DMEM) supplemented with 10% fetal bovine serum and 1% penicillin-streptomycin in a 5% $CO_2$ incubator. U2OS p53-shRNA and U2OS Ctrl-shRNA cells were generated as described in Li, P. et al., Regulation of p53 target gene expression by peptidylarginine deiminase 4. *Mol Cell Bial* 28 (15), 4745-4758 (2008). Concentrations and duration of YW3-56 treatment were performed as specified in the figures and text. For starvation assay, U2OS cells were first cultured in serum-free DMEM for 16 hr, 10% fetal bovine serum and different concentrations of YW3-56 was then added back and cells were further incubated for 8 hr before further analyses. SESN2 siRNA (Santa Cruz) and GFP siRNA (Dharmacon Inc.) were transfected into U2OS cells using the XtremeGene siRNA transfection reagents (Roche Inc.). Cells were incubated in the presence of the siRNA for 48 hr before adding YW3-56 and further incubated for 8 hr before analyses.

Figure 14A:
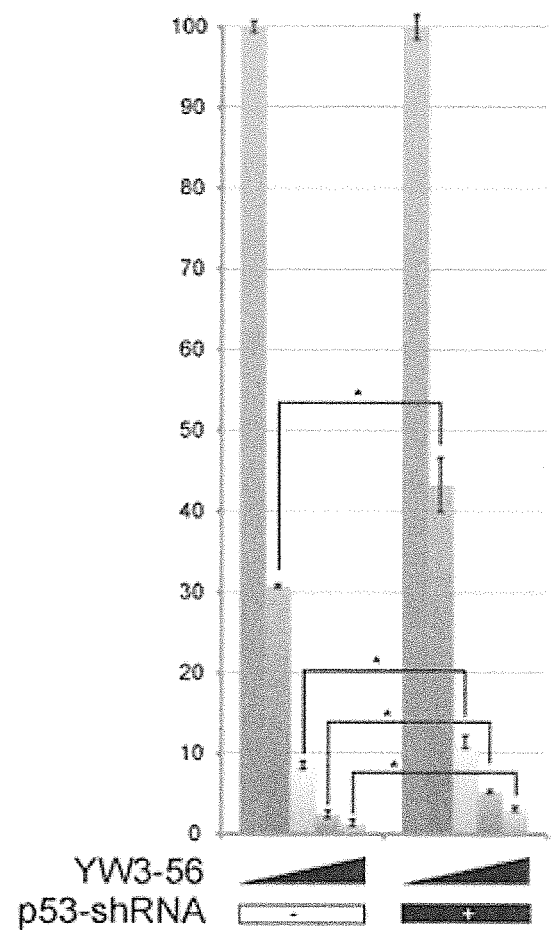
FIG. 14A is a graph showing results of MTT assays of growth inhibition of U2OS cells treated with a PAD4 inhibitor and without or with p53 depletion by shRNA.

Comparing cells treated with the inhibitor at the same concentration, the efficacy of YW3-56 on cell growth inhibition is decreased significantly after p53 depletion. FIG. 14A, MTT assays of growth inhibition of U2OS cells without or with p53 depletion by shRNA, * indicates p<0.02.

Figure 14B:
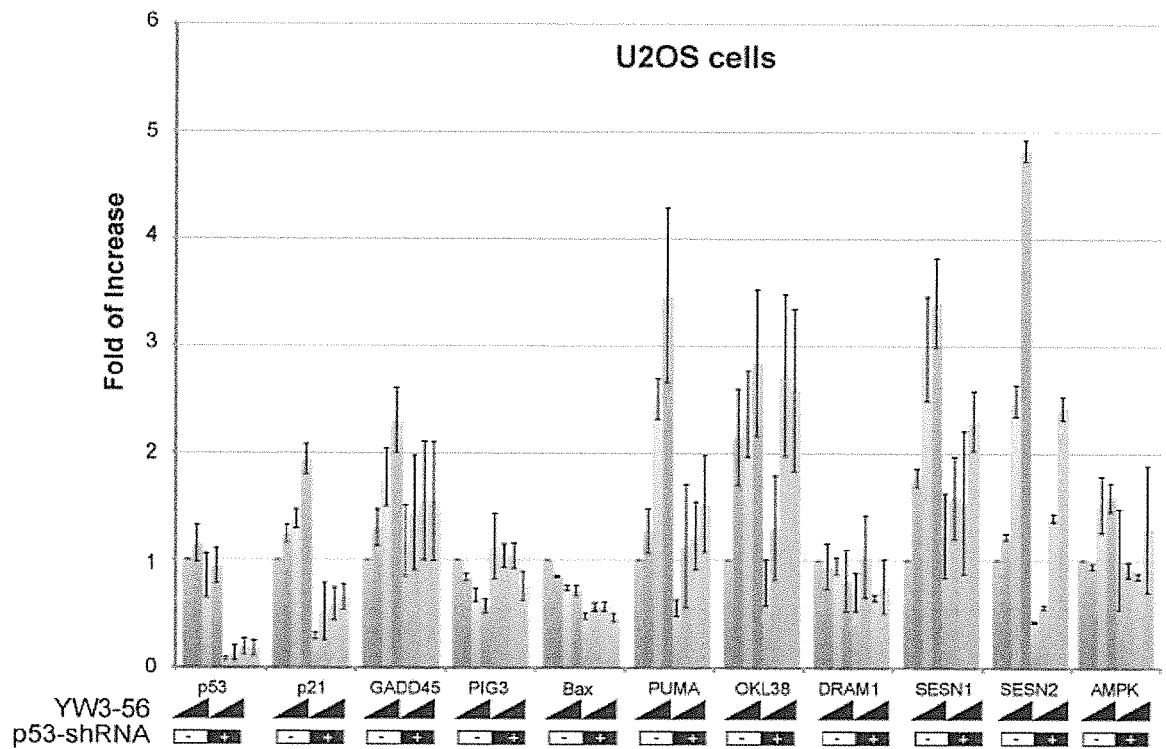
FIG. 14B is a graph showing effects of PAD4 inhibitor treatment of U2OS cells on expression of the indicated proteins.

The decrease in p53 mRNA and protein is confirmed by reverse transcription-quantitative PCR (RT-qPCR) analyses and Western blot. FIG. 14B, shows effects of YW3-56 on p53 and its target gene expression analyzed using the reverse transcription quantitative PCR (RT-qPCR) method.

In response to DNA damage, starvation, and stress signals, p53 activates many downstream tumor suppressor genes to regulate cell cycle arrest, apoptosis, and autophagy. To identify the molecules linking YW3-56 treatment with cell growth inhibition, RT-qPCR and Western blot assays are performed. YW3-56 treatment increases the expression of cell cycle inhibitory genes and proapoptotic genes (e.g., PUMA) in a drug dosage- and p53-dependent manner at both mRNA and protein levels.

Because the prominent effects of YW3-56 treatment are autophagy induction, a molecular link between YW3-56 treatment and autophagy is investigated.

Furthermore, the aptitude of basal and induced expression of Sestrin1 and 2 is decreased in p53 depletion cells at both mRNA and protein levels.

A high concentration of YW3-56 is still capable of inducing Sestrin1 and 2 in cells with p53 depletion suggesting that these promoters are activated after YW3-56 treatment by lower levels of p53 or possibly other factors.

Figure 14C:
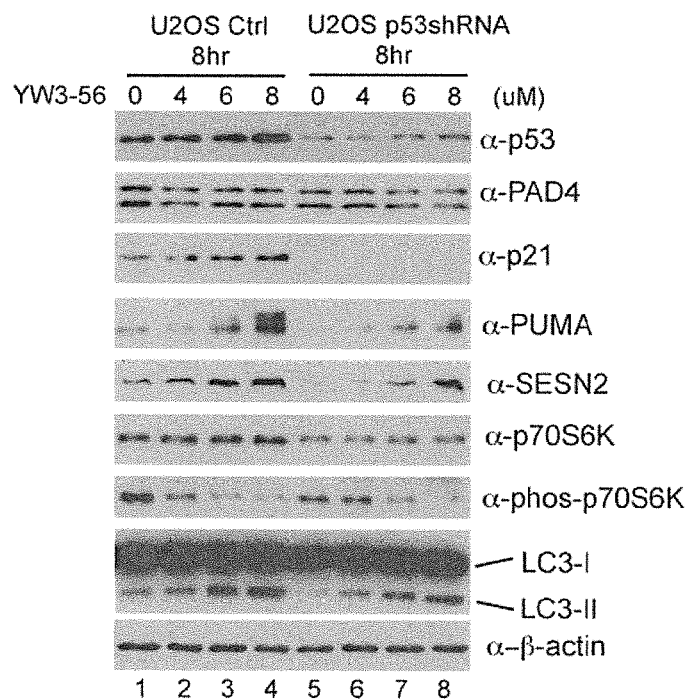
FIG. 14C is an image of a Western blot showing effects of PAD4 inhibitor treatment of U2OS cells on p53 and its target gene expression analyzed using reverse transcription quantitative PCR (RT-qPCR) method.

FIG. 14C, shows the induction of p21, PUMA, and Sestrin2 expression detected after YW3-56 treatment in U2OS cells with or without p53 depletion. Concomitant with Sestrin2 induction, p70S6K phosphorylation is inhibited and LC3 cleavage is induced.

Figure 14D:
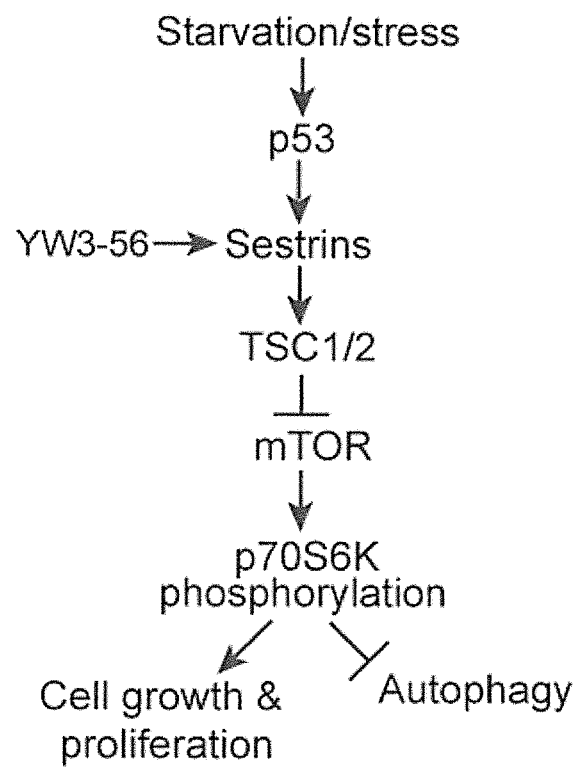
FIG. 14D is a schematic diagram showing the p53-sestrin2-mTOR signaling pathway linking a PAD4 inhibitor to autophagy.

FIG. 14D shows an illustration of the p53-sestrin2-mTOR signaling pathway. Sestrin2 forms complex with TSC1/2 to inhibit mTOR signaling and subsequent p70S6K phosphorylation thereby offering a molecular mechanism linking YW3-56 treatment to autophagy.

p53 directly binds the SESN2 promoter to regulate its expression.

Chromatin immunoprecipitation experiments are performed to test if p53 and histone Arg modifications directly regulate Sesn2 gene promoter. ChIP experiments were carried out essentially as described in Li, P. et al., Mol. Cell Biol., 28 (15), 4745-4758 (2008). Antibodies used in ChIP were: anti-p53 (Sigma), anti-PAD4, anti-H3Cit (Abcam), anti-H3R17Me (Abcam). Multiple pairs of primers spanning different regions of Sesn2 are designed to identify a p53 binding site at the Sesn2 gene. p53 binding is relatively abundant at the +733 position in untreated U2OS cells, while its binding to this site is dramatically elevated after DNA damage induced by UV irradiation. After 8 hr YW3-56 treatment, p53 binding at the +733 position of Sesn2 is increased >4-fold with a concomitant increase of histone H3 Arg17 methylation (H3R17Me) (FIG. 14G, upper panel). In contrast, after YW3-56 treatment, a decrease in PAD4 binding and histone H3 citrullination (H3Cit) at the +733 position is consistently detected. ChIP results support a model in which p53 associates with while PAD4 dissociates from the Sesn2 promoter after YW3-56 treatment, allowing a decrease in H3Cit and an increase in H3R17Me to facilitate Sesn2 expression.

Several p53 target genes, including DRAM, Sestrin1 and 2, have been implicated in mediating autophagy after p53 activation. FIG. 14B shows that DRAM mRNA is not altered after YW3-56 treatment in U2OS cells. In contrast, sestrin1 and 2 mRNA (FIG. 14B) and Sestrin2 protein levels (FIG. 14C) are significantly increased after YW3-56 treatment in a concentration dependent manner.

Figure 14E:
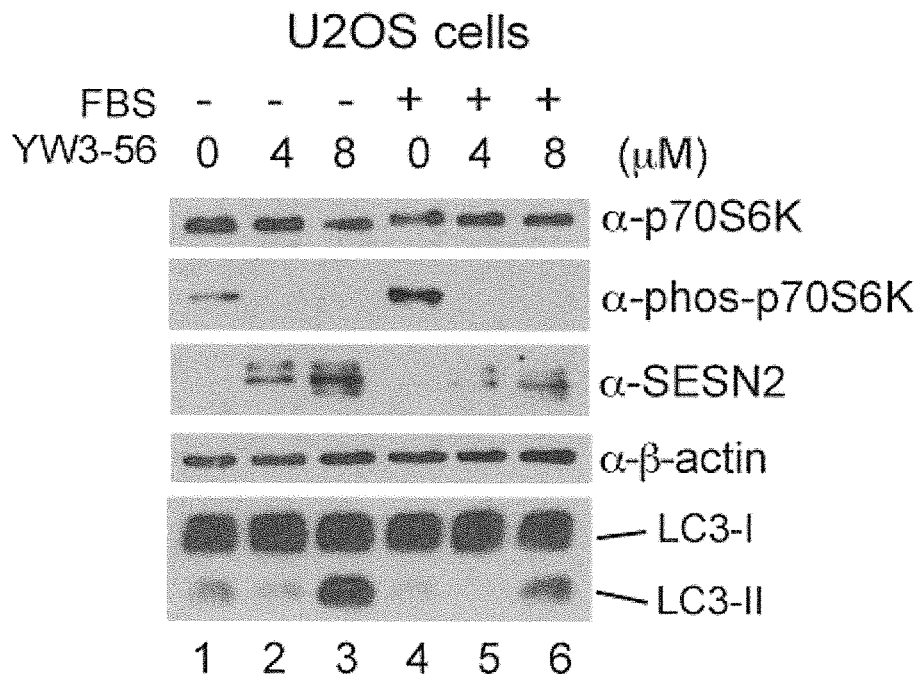
FIG. 14E is an image of a Western blot showing effects of a PAD4 inhibitor on U2OS cells upon serum starvation or stimulation.
Figure 14F:
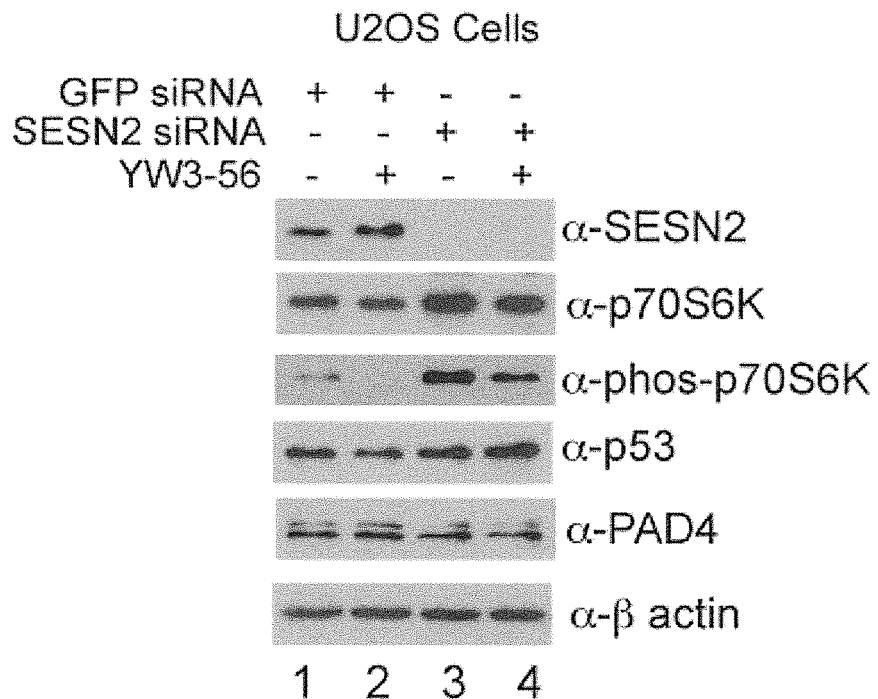
FIG. 14F is an image of a Western blot showing effects of Sestrin2 depletion on p70S6K phosphorylation before and after YW3-56 treatment.
Figure 14G:
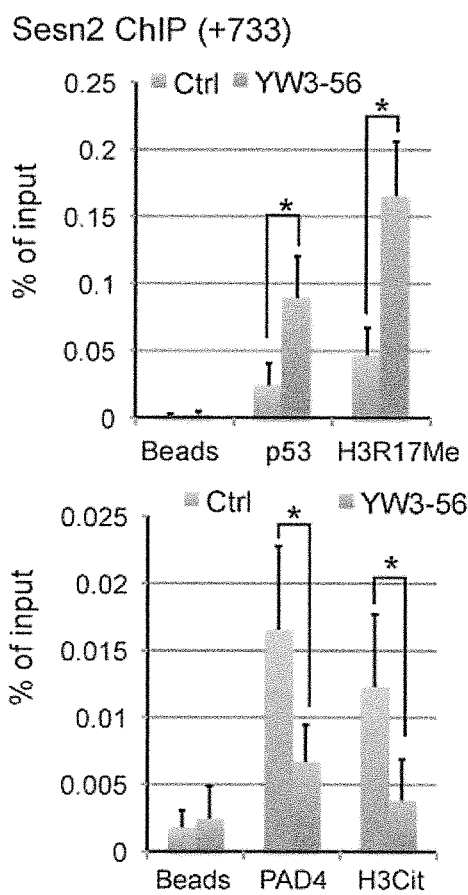
FIG. 14G is shows ChIP analyses of p53 and PAD4 association as well as histone H3R17Me and H3Cit modifications at the sestrin2 promoter before and after YW3-56 treatment at 8 μM for 8 hr.

FIG. 14E shows induction of Sestrin2 and inhibition of p70S6K phosphorylation by YW3-56 in U2OS cells upon serum starvation or stimulation. FIG. 14F shows the effects of Sestrin2 depletion on p70S6K phosphorylation before and after YW3-56 treatment.

FIG. 14G, ChIP analyses of p53 and PAD4 association as well as histone H3R17Me and H3Cit modifications at the sestrin2 promoter before and after YW3-56 treatment at 8 μM for 8 hr. Averages and standard deviations (n=2×3) are shown (*indicate p<0.005).

Example 16

Induction of p53 and its target gene expression by YW3-88 and BL1-07.

Figure 15A:
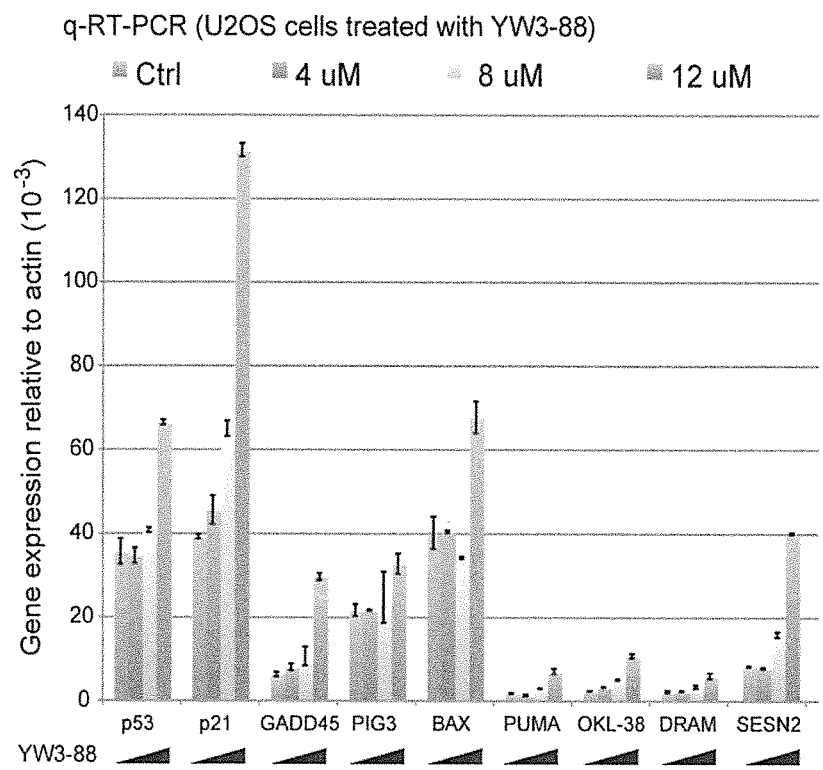
FIG. 15A is a graph showing changes in mRNA levels of p53, PUMA and p21 proteins after treatment of cancer cells with a PAD4 inhibitor.
Figure 15B:
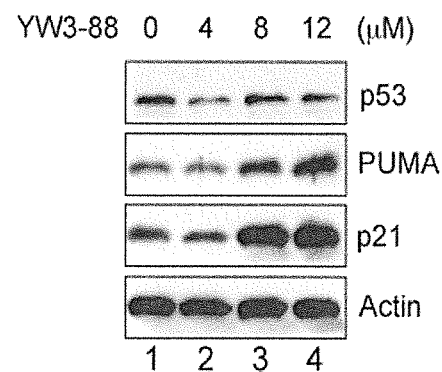
FIG. 15B is an image of a Western blot showing changes in p53 and its target genes after treatment of cancer cells with a PAD4 inhibitor.
Figure 15C:
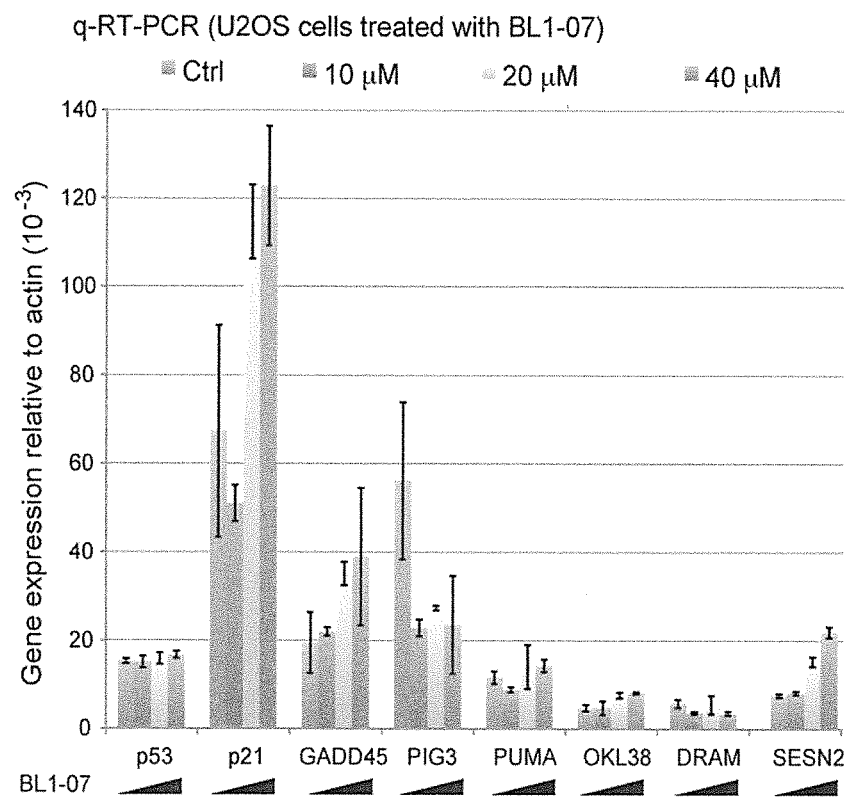
FIG. 15C is a graph showing changes in mRNA levels of p53, PUMA and p21 proteins after treatment of cancer cells with a PAD4 inhibitor.

FIG. 15A shows changes in the mRNA levels of p53 and its target gene after treatment with YW3-88 at different concentrations in U2OS cells are measured using RT-qPCR analyses. The relative abundance of each gene is compared with β-actin as a reference. Increase in several p53 target genes, such as p21, GADD45, PUMA, OKL38, DRAM, and Sestrin2, is detected after YW3-88 treatment at 12 μM concentration. FIG. 15B shows amounts of p53, p21, and PUMA proteins in U2OS cells after YW3-88 treatment are analyzed by Western blot. Increase in p21 and PUMA proteins is detected. FIG. 15C shows changes in mRNA levels of p53 and its target gene after treatment with BL1-07 at different concentrations in U2OS cells are measured using RT-qPCR analyses. Consistent with its higher dose requirement for cell killing, BL1-07 is less potent to induce p53 and its target genes even at higher concentrations.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of inhibiting peptidylarginine deiminase 4 (PAD4) activity in a subject, comprising:
administering a therapeutically effective amount of a composition comprising a compound having the structural formula selected from the group consisting of:

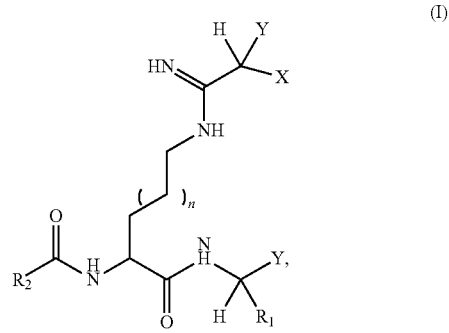

where n is 1 or 2; X is halogen; each Y is independently H, halogen, an O-linked aliphatic substituent or an N-linked aliphatic substituent; $R_1$ is an aromatic substituent; and $R_2$ is an aliphatic or aromatic substituent;

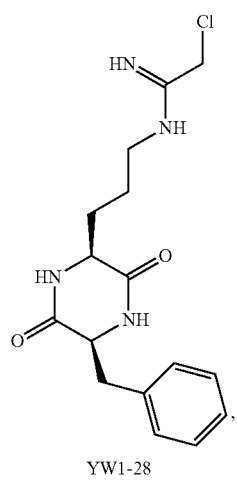
YW1-28 (3)
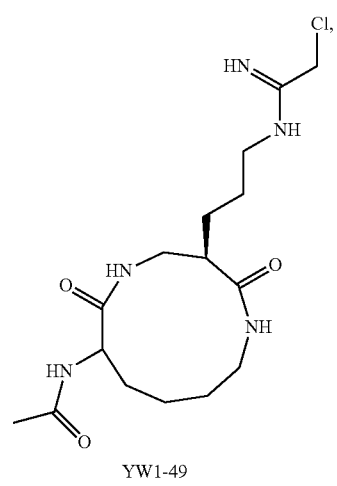
YW1-49 (6)
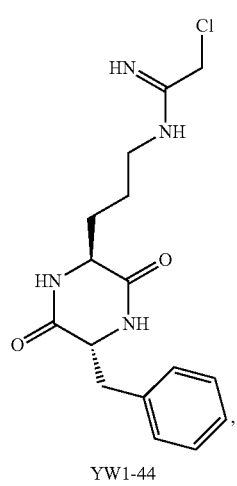
YW1-44 (4)
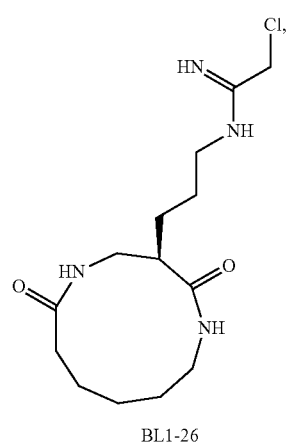
BL1-26 (7)
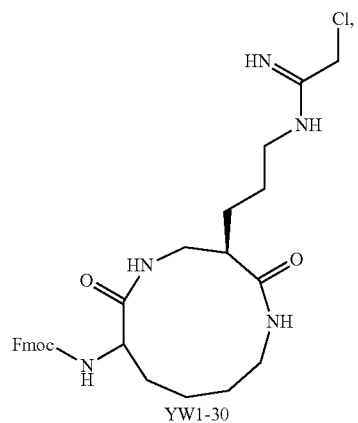
YW1-30 (5)
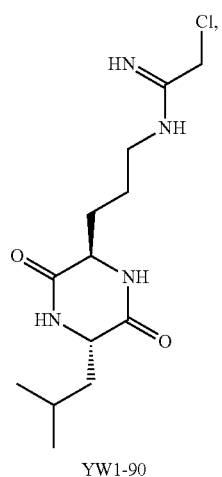
YW1-90 (8)

(9)
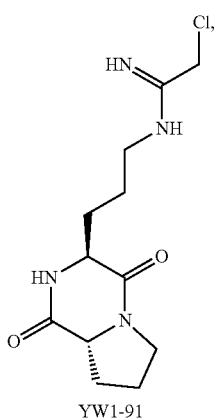
YW1-91
(10)
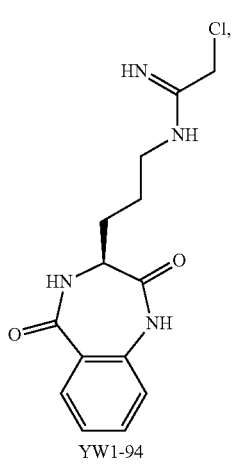
YW1-94
(11)
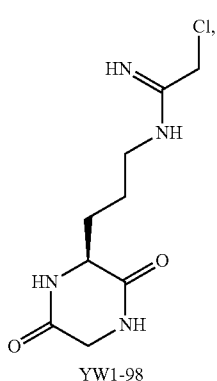
YW1-98
(12)
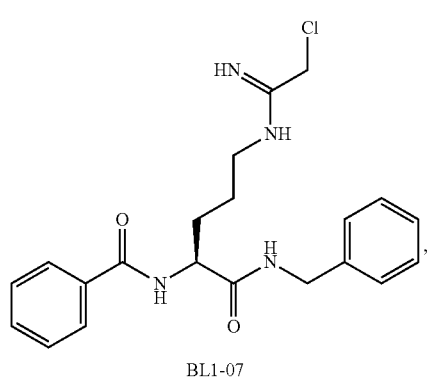
BL1-07
(13)
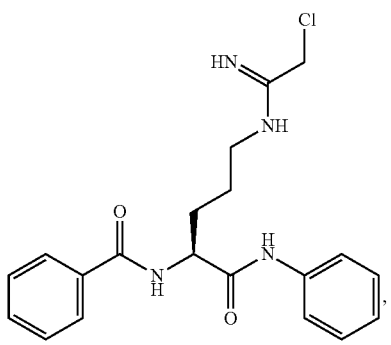
BL1-15
(15)
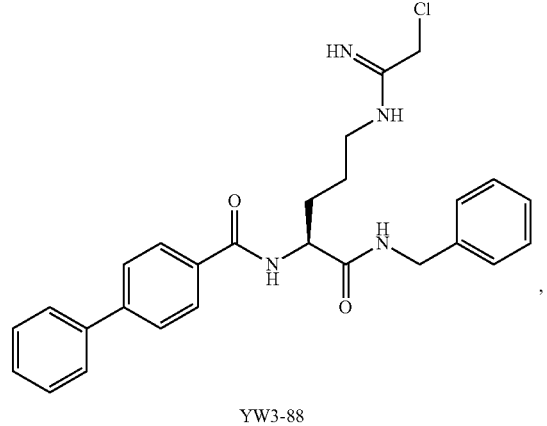
YW3-88
(16)
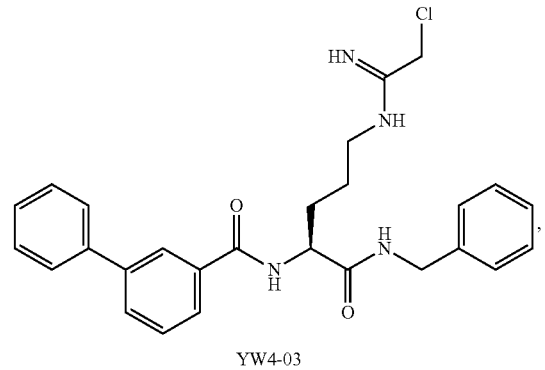
YW4-03
(17)
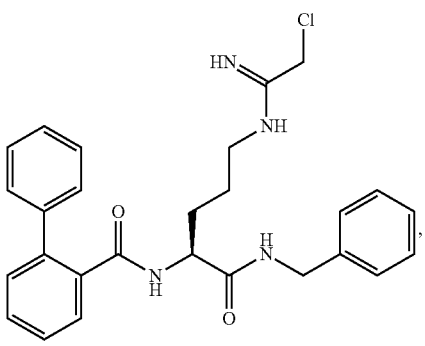
YW4-06

-continued

(18)
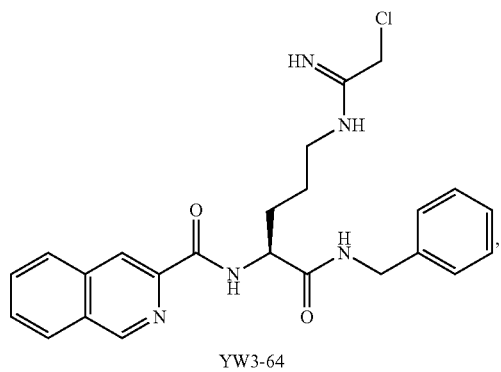
YW3-64

(19)
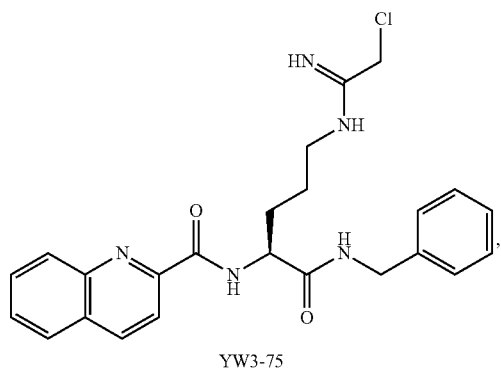
YW3-75

(20)
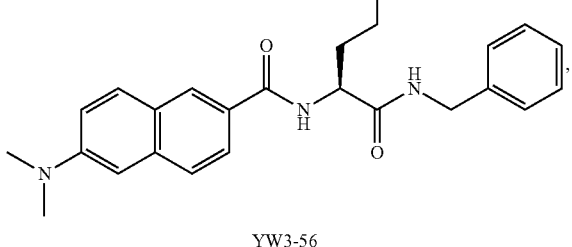
YW3-56

(21)
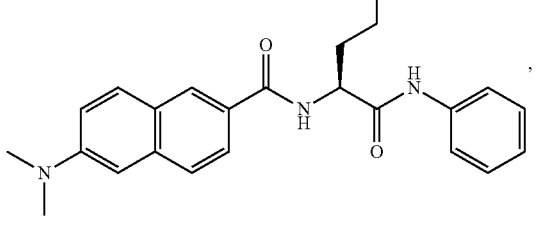
YW3-71

-continued

(23)
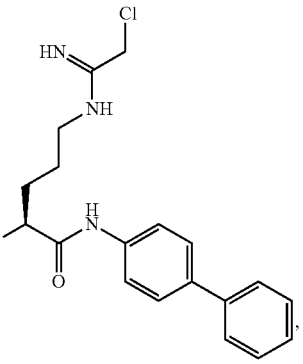
YW3-92

(24)
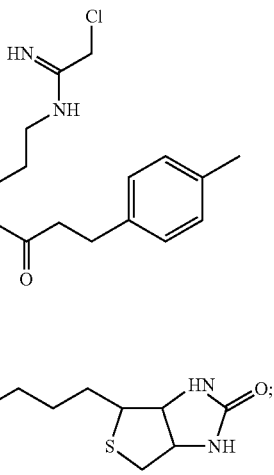
YW3-92

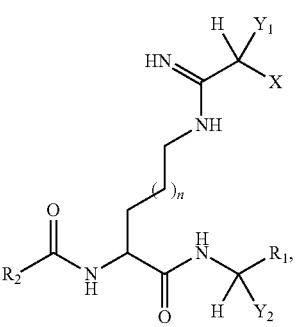
YW4-15 a salt, stereoisomer, hydrate, amide or ester thereof; and a mixture of any two or more thereof.

2. The method of claim 1, wherein the composition comprises a compound selected from the group consisting of: YW3-56F, YW3-56Br, YW-56A, YW3-56A-F, YW3-56A-Br.

3. The method of claim 1, wherein the composition comprises a compound having the structural formula:

(III)

where n is 1 or 2; X is halogen; $Y_1$ and $Y_2$ are each independently H, halogen, an O-linked aliphatic substituent or an N-linked aliphatic substituent; $R_1$ is an aromatic substituent; and $R_2$ is an aliphatic or aromatic substituent.

4. The method of claim 3, wherein n is 1, $Y_1$ and $Y_2$ are both H and X is F or Cl.

5. The method of claim 4, wherein the compound is selected from the group consisting of:
(12) BL1-07
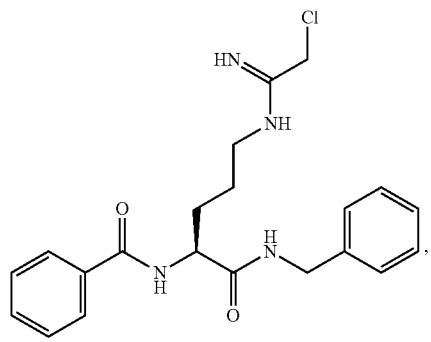
(13) BL1-15
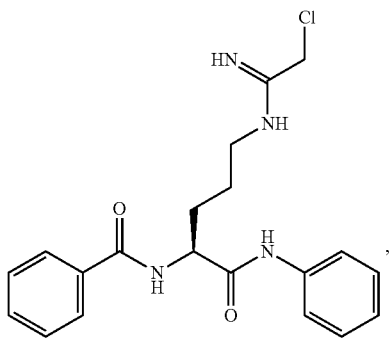
(15) YW3-88
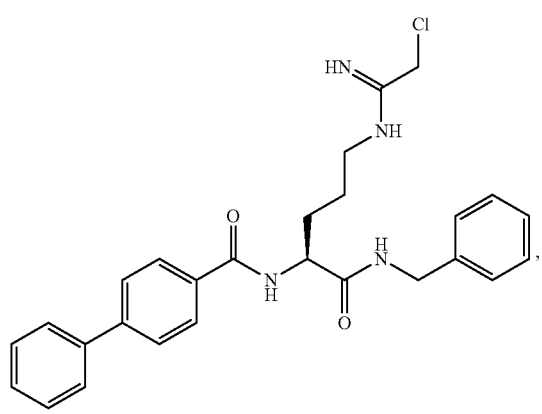
(16) YW4-03
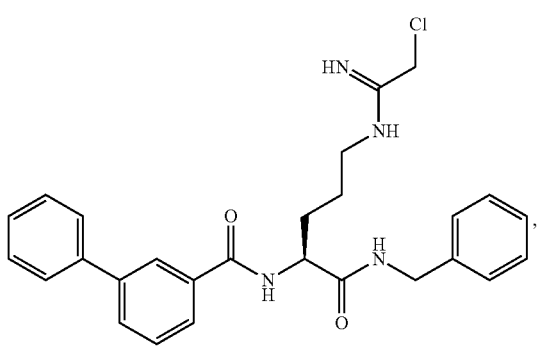
(17) YW4-06
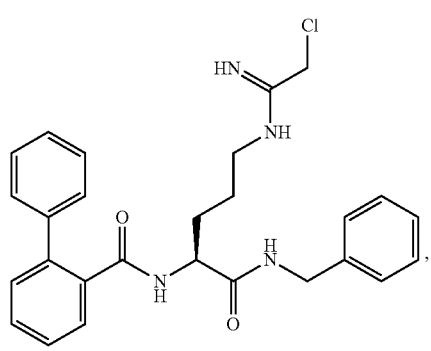
(18) YW3-64
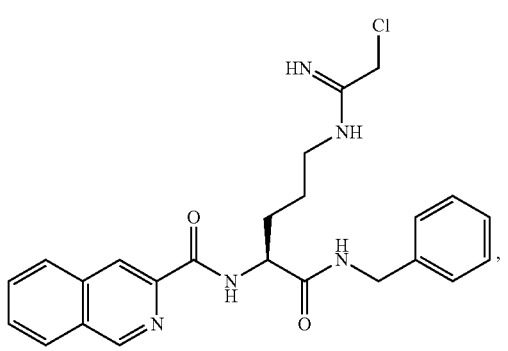
(19) YW3-75
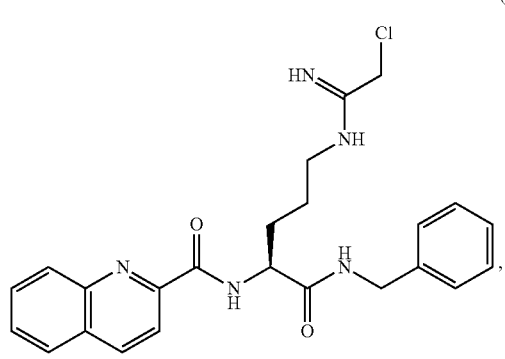
(20) YW3-56
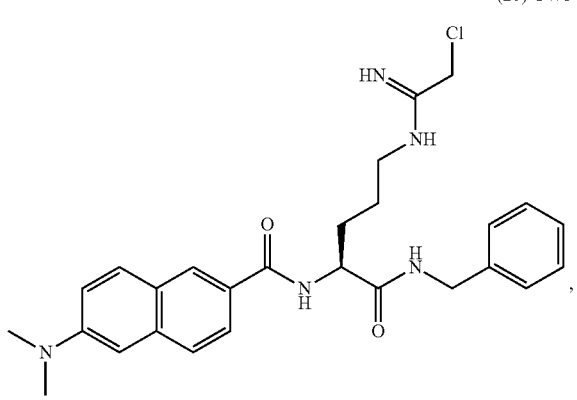

-continued

(21) YW3-71

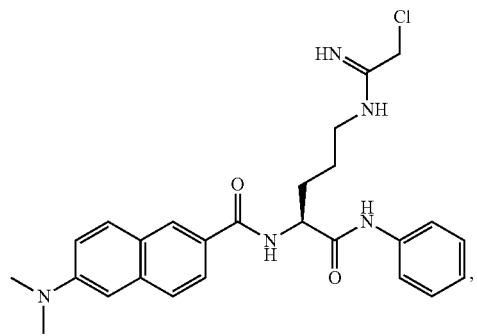

(23) YW3-92

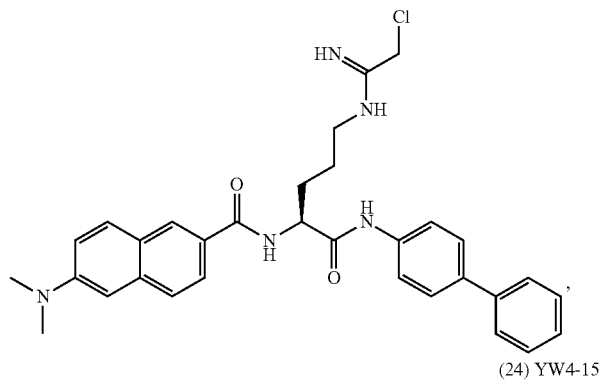

(24) YW4-15

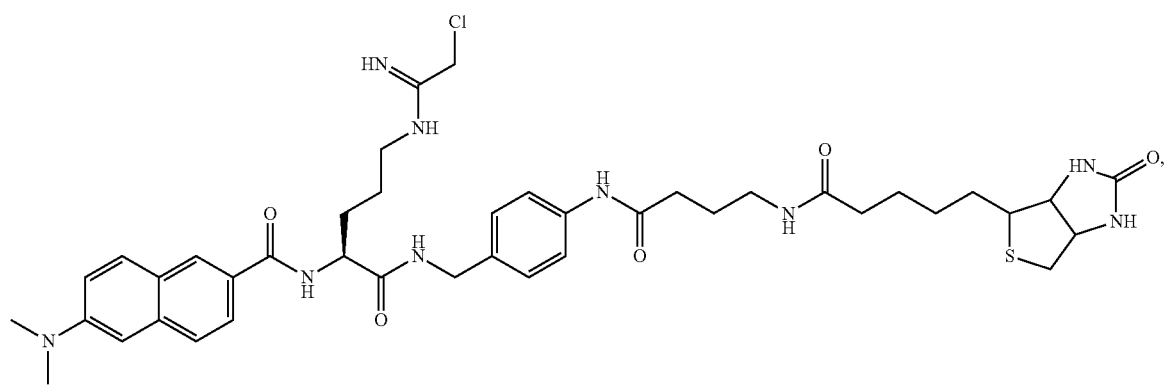

YW3-56, YW3-56F, YW3-56Br, YW3-56A, YW3-56A-F, YW3-56A-Br; a salt, stereoisomer, hydrate, amide or ester thereof; and a mixture of any two or more thereof.

6. The method of claim 1 wherein the subject is human.

7. The method of claim 1 wherein the subject has or is at risk of having cancer.

8. The method of claim 7 wherein the cancer is characterized by decreased levels or activity of one or more tumor suppressors.

9. The method of claim 8 wherein the tumor suppressor is p53.

10. The method of claim 1, wherein administering the therapeutically effective amount of the composition to a subject detectably increases autophagy and/or decreases proliferation of cells of the cancer.

11. The method of claim 1, further comprising administration of an additional therapeutic agent, an adjunct anti-cancer treatment or both an additional therapeutic agent and an adjunct anti-cancer treatment.

12. The method of claim 11, wherein the additional therapeutic agent comprises administration of a histone deacetylase inhibitor.

13. The method of claim 12, wherein the histone deacetylase inhibitor is SAHA.

14. The method of claim 1 wherein the subject has or is at risk of having an autoimmune disease.

* * * * *